(12) United States Patent
Thiruvengadam et al.

(10) Patent No.: US 7,425,410 B2
(45) Date of Patent: Sep. 16, 2008

(54) METHODS FOR DIAGNOSING A BIPOLAR DISORDER AND UNIPOLAR DISORDER

(75) Inventors: Alagu P. Thiruvengadam, Ellicott City, MD (US); Krish Chandrasekaran, Columbia, MD (US)

(73) Assignee: Free State Diagnostics, LLC, Ellicott City, MD (US)

( * ) Notice: Subject to any disclaimer, the term of this patent is extended or adjusted under 35 U.S.C. 154(b) by 422 days.

(21) Appl. No.: 10/823,647

(22) Filed: Apr. 14, 2004

(65) Prior Publication Data

US 2005/0095579 A1 May 5, 2005

Related U.S. Application Data

(60) Provisional application No. 60/515,846, filed on Oct. 30, 2003.

(51) Int. Cl.
- *C12Q 1/34* (2006.01)
- *C12Q 1/00* (2006.01)
- *G06F 19/00* (2006.01)
- *G01N 33/48* (2006.01)
- *G01N 33/50* (2006.01)

(52) U.S. Cl. ............ 435/4; 435/29; 435/366; 424/9.1; 424/93.1; 424/93.7; 702/19

(58) Field of Classification Search ............ 435/29, 435/366; 424/9.1, 93.1, 93.7; 702/19
See application file for complete search history.

(56) References Cited

OTHER PUBLICATIONS

Cloning: Present Uses and Promises. http://ospp.od.nih.gov/policy/cloning.asp (p. 3, lines1-2).*
Buss et al. Lymphoblastoid transmembrane potential in bipolar patients, their siblings, and unrelated healthy comparison subjects. Psychiatry Research 1996 59:197-201.*
El-Mallakh et al. Leukocyte transmembrane potential in bipolar illness. J Affect Disord. Nov. 4, 1996;41(1):33-7.*
De Fusco et al. Haploinsufficiency of ATP1A2 encoding the Na+/K+ pump alpha2 subunit associated with familial hemiplegic migraine type 2. Nat Genet. Feb. 2003;33(2):192-6. Epub Jan. 21, 2003.*
El-Mallakh et al. (1996) Leukocyte transmembrane potential in bipolar illness. J. Affect. Disord. 41:33-34.*
Garrahan et al. 1967. The Behaviour of the Sodium Pump in Red Cells in the Absence of External Potassium. J. Physiol. 192:159-174.*
Antia et al. 1995. The upregulation of Na+, K+-ATPase pump numbers in lymphocytes from the first-degree unaffected relatives of patients with manic depressive psychosis in response to in vitro lithium and sodium ethacrynate. J. Affect. Disord. 34:33-39.*

\* cited by examiner

*Primary Examiner*—Blaine Lankford
*Assistant Examiner*—Taeyoon Kim
(74) *Attorney, Agent, or Firm*—Sughrue Mion, PLLC

(57) ABSTRACT

Changes that occur in Na+K+ ATPase regulation and therefore in the membrane potential in cells from bipolar individuals, as compared to cells from unaffected control individuals, are utilized to provide a diagnostic assay for a bipolar disorder. The diagnostic assay may also or instead exploit the similarity of cells from bipolar patients to those of people already known to have a bipolar disorder. A similar diagnostic assay is provided for diagnosing unipolar disorder. The diagnostic assays may further involve manipulation of membrane potential by incubation of cells in K+-free buffer and/or incubation with one or more compounds that alter Na+K+ ATPase activity. Although a variety of cells may be used, the diagnostic assays preferably employ lymphoblasts or whole blood cells.

4 Claims, 15 Drawing Sheets

95 percent confidence interval for difference of means: -159.577 to -66.090
The difference in the mean values of the two groups is greater than
would be expected by chance; there is a statistically significant difference
between the input groups (P = <0.001).
Power of performed test with alpha = 0.050: 0.999

Ethacrynate Induced Changes in Membrane Potential

Cells were incubated for 30 min in presence or absence of ethacrynate in regular buffer or in K+ free buffer.

Relative Intensity Ratio = Intensity Ratio in $K^+$ Free Buffer / Intensity Ratio in Regular Buffer Relative Rate of polarization = Polarization Ratio in $K^+$ Free Buffer / Polarization Ratio in Regular Buffer

Effect of Monensin on Membrane Potential
Cells were incubated for 30 min in K$^+$ Free Buffer with or without monensin (10 μM).

Effect of PMA on the Relative Rate of Repolarization Cells were incubated in regular or K⁺free buffers with or without PMA (2 μM) for 30 min.

**Effect of Lithium on Membrane Potential
Cells were incubated in Regular or in K⁺Free Buffer
for 2 hours with or without LiCl (20 mM).**

EXAMPLE OF ANOVA TO DIAGNOSE A BIPOLAR PATIENT
PATIENT-A IS BIPOLAR

METHODS FOR DIAGNOSING A BIPOLAR DISORDER AND UNIPOLAR DISORDER

This application claims the benefit of U.S. Provisional Application No. 60/515,846, filed Oct. 30, 2003, incorporated herein by reference.

FIELD OF THE INVENTION

The present invention relates to a method for diagnosing a bipolar disorder. In particular, this method utilizes changes that occur in $Na^+K^+$ ATPase regulation in cells from bipolar individuals, as compared to cells from unaffected control individuals, to provide a diagnostic assay for a bipolar disorder. The present invention also relates to a method for diagnosing unipolar disorder.

BACKGROUND OF THE INVENTION

Mental illness afflicts nearly ten percent of the general population both in the United States and in the rest of the world. Bipolar (manic depressive) disorders occur in one to two percent of the population and are the sixth leading cause of disability (Coryell et al., *Am. J. Psychiatry* 150:720-727 (1993); Lopez, A. D., and Murray, C. C., *Nat. Med.* 4:1241-1243 (1998); Hyman, S. E., *Am. J. Geriatr. Psychiatry* 9:330-339 (2001)). A problem facing the medical community is misdiagnosis of a bipolar disorder. Misdiagnosed patients receive an average of 3.5 misdiagnoses and consult four physicians before receiving an accurate diagnosis ("Living with bipolar disorder: How far have we really come?" National Depressive and Manic-Depressive Association, Chicago, Ill. (2001)).

The current diagnostic method for a bipolar disorder (bipolar disorder I and II) involves a series of clinical interviews and examination using the *Diagnostic and Statistical Manual of Mental Disorders* (DSM-IV), the main diagnostic reference of Mental Health professionals in the United States, which is now in its fourth edition. Significant controversy exists about the validity of this manual, which limits the accuracy of clinical diagnosis (Torrey et al, "Surviving Manic Depression", *Basic Books*, New York (2002)). In addition, attempts are underway to identify the genes underlying these illnesses and thereby develop diagnostic markers. However, their identification and possible use as diagnostic markers are years away (Bradbury, J., *Lancet* 357:1596 (2001)).

The lifetime risk for unipolar disorder (major depressive disorder) is 10% to 25% for women and from 5% to 12% for men. At any point in time, 5% to 9% of women and 2% to 3% of men suffer from this disorder. Prevalence is unrelated to ethnicity, education, income, or marital status.

Like bipolar disorders, unipolar disorder is also currently diagnosed using the DSM-IV. By definition, unipolar disorder and bipolar disorders are distinct conditions. Unipolar disorder is diagnosed when there has never been a manic episode and at least five of the following symptoms have been present during the same 2 week depressed period:
Abnormal depressed mood.
Abnormal loss of all interest and pleasure.
Appetite or weight disturbance, either:
  Abnormal weight loss (when not dieting) or decrease in appetite.
  Abnormal weight gain or increase in appetite.
Sleep disturbance, either abnormal insomnia or abnormal hypersomnia.
Activity disturbance, either abnormal agitation or abnormal slowing (observable by others).
Abnormal fatigue or loss of energy.
Abnormal self-reproach or inappropriate guilt.
Abnormal poor concentration or indecisiveness.
Abnormal morbid thoughts of death or suicide.

There is evidence that unipolar disorder is, in part, a genetic disorder. Therefore, as with bipolar disorders, attempts are underway to identify the genes underlying unipolar disorder and thereby develop diagnostic markers. However, this has yet to be achieved.

In virtually every animal cell, the concentration of $Na^+$ in the cell (~12 mM) is lower than the concentration of $Na^+$ in the surrounding medium (~145 mM), and the concentration of $K^+$ in the cell (~140 mM) is higher than the concentration of $K^+$ in the surrounding medium (~4 mM). This imbalance is established and maintained by an active transport system in the plasma membrane. The transporter enzyme $Na^+K^+$ ATPase, also known as the sodium pump, couples breakdown of ATP to the simultaneous movement of both $Na^+$ and $K^+$ against their electrochemical gradients. For each molecule of ATP hydrolyzed to ADP and $P_i$, the $Na^+K^+$ ATPase transports two $K^+$ ions inward and three $Na^+$ ions outward across the plasma membrane.

The $Na^+K^+$ ATPase is an integral protein with two subunits (Mr ~50,000 and ~110,000), both of which span the membrane. A proposed mechanism by which ATP hydrolysis is coupled to ion transport involves the $Na^+K^+$ ATPase cycling between two forms, a phosphorylated form with high affinity for $K^+$ and low affinity for $Na^+$, and a dephosphorylated form with high affinity for $Na^+$ and low affinity for $K^+$. The conversion of ATP to ADP and $P_i$ occurs in two steps catalyzed by the enzyme.

In addition to the $Na^+K^+$ ATPase, the plasma membrane also contains channel proteins that allow the principal cellular ions ($Na^+$, $K^+$, $Ca^{2+}$, and $Cl^-$) to move through them at different rates down their concentration gradients. Ion concentration gradients generated by pumps and selective movement of ions through channels constitutes the principal mechanism by which a difference in voltage, or electric potential, is generated across the plasma membrane. However, because the plasma membranes of animal cells contain many open $K^+$ channels, and relatively few open $Na^+$, $Ca^{2+}$, and $Cl^-$ channels, the membrane potential in animal cells depends largely on open $K^+$ channels. As a result, the major ionic movement across the plasma membrane is that of $K^+$ from the inside outward, powered by the $K^+$ concentration gradient, leaving an excess of negative charge on the inside and creating an excess of positive charge on the outside.

The magnitude of this membrane potential generally is −50 mV to −70 mV (with the inside of the cell negative relative to the outside), which is characteristic of most animal cells and essential to the conduction of action potentials in neurons. As noted earlier, the $K^+$ concentration gradient that drives the flow of $K^+$ ions through open $K^+$ channels is generated by the $Na^+K^+$ ATPase. The central role of the $Na^+K^+$ ATPase is reflected in the energy invested in this reaction: about 25% of the total energy consumption of a human at rest.

The steroid derivative ouabain is a potent and specific inhibitor of the $Na^+K^+$ ATPase. Ouabain and another steroid derivative, digitoxigenin, are the active ingredients of digitalis, which has long been used to treat congestive heart failure. Inhibition of the $Na^+K^+$ ATPase by digitalis leads to an increased $Na^+$ concentration in cells, activating a $Na^+Ca^{2+}$ antiporter in cardiac muscle. The increased influx of $Ca^{2+}$ through this antiporter produces elevated cytosolic $Ca^{2+}$, which strengthens the contractions of heart muscle.

The $Na^+K^+$ ATPase has also been investigated for its possible involvement in bipolar disorder pathophysiology (El- Mallakh et al, *Biol. Phychiatry,* 537:235-244 (1995)). However, this has been an unsettled and controversial subject in the field for many years. $Na^+K^+$ ATPase activity has been variously reported to be increased, decreased, or unchanged in bipolar patients. In 1997, Looney et al conducted a meta-analysis of the available literature on erythrocyte $Na^+K^+$ ATPase activity in bipolar disorders and concluded that it is lower in bipolar patients (Looney et al, *Depress. Anxiety,* 5:53-65 (1997)). However, the question of exactly how the $Na^+K^+$ ATPase plays a role in bipolar disorders remains unanswered.

Lithium, an alkaline metal that has been used successfully for over fifty years to stabilize mood in bipolar disorders, has been shown to augment $Na^+K^+$ ATPase activity. Recently, the role of lithium in depolarizing the resting membrane potential of neurons has been analyzed (Thiruvengadam, *J. Affect. Disord.,* 65:95-99 (2001); and Thiruvengadam, "Electro-biochemical coupling, excitability of neurons and bipolar disorder, *Bipolar Disorder* 3 (2001)). Hyperpolarization of membrane potential in leukocytes of bipolar patients and depolarization following the addition of lithium has been observed (El Mallakh et al, *J. Affect. Disord.,* 41:33-37 (1996)). In addition, a significantly smaller increase in $Na^+K^+$ ATPase density after incubation for 72 hours in ethacrynate or lithium has been observed in cells of bipolar patients compared to cells of unaffected individuals (Wood et al, *J. Affect. Disord.,* 21:199-206 (1991)).

El-Mallakh et al measured the transmembrane potential in leukocytes from hospitalized bipolar patients and observed that the transmembrane potential of the bipolar patients was hyperpolarized compared with normal controls and euthymic patients on lithium (El-Mallakh et al, *J. Affect. Disord.,* 41:33-37 (1996)). However, Buss et al measured the membrane potentials of cultured lymphoblasts and concluded that there was no significant difference in membrane potentials among bipolar patients, their siblings and normal controls (Buss et al, *Psychiatry Res.* 59:197-201 (1996)).

In view of the previously studies on the possible involvement of the $Na^+K^+$ ATPase in bipolar disorders, one would not expect $Na^+K^+$ ATPase activity to serve as a reliable basis for diagnosing a bipolar disorder in an individual patient, because measurements of $Na^+K^+$ ATPase activity are highly variable. Similarly, one would not expect transmembrane potential to serve as a reliable basis for diagnosing a bipolar disorder in an individual patient, because measurements of transmembrane potential are highly variable.

Accordingly, despite the existence of treatments for bipolar disorders and unipolar disorder and recent advances in the psychiatric field, there remains a heretofore unmet need for clinical tests to augment the DSM-IV in diagnosing bipolar disorders and unipolar disorder.

SUMMARY OF THE INVENTION

The present invention exploits changes that take place in $Na^+K^+$ ATPase regulation in cells of bipolar patients, as compared to cells of normal, unaffected control subjects, to provide a diagnostic assay for a bipolar disorder. The present invention provides a reliable diagnostic assay to differentiate cells from bipolar patients from those of normal, unaffected individuals, schizophrenic individuals, and unipolar (depressive) individuals. The diagnostic assay of the invention may also or instead exploit the similarity of cells from bipolar patients to those of people already known to have a bipolar disorder. Thus, the present invention addresses the heretofore unmet need for a clinical test useful in the diagnosis of a bipolar disorder.

The present invention further provides a diagnostic assay useful in differentiating cells from unipolar (depressive) patients from those of normal, unaffected individuals, schizophrenic individuals, and bipolar individuals. This diagnostic assay may also or instead exploit the similarity of cells from unipolar patients to those of people already known to have unipolar disorder.

As shown herein, the membrane potential in cultured cells from bipolar patients is significantly different than the membrane potential in cultured cells from unaffected controls and siblings. For example, the membrane potentials of bipolar lymphoblasts are significantly hyperpolarized when compared with those of siblings and negative controls. The changes in membrane potential reflect changes in $Na^+K^+$ ATPase regulation that occur in cells of patients affected with a bipolar disorder.

In preferred embodiments, a diagnostic assay for a bipolar disorder according to the invention utilizes changes in membrane potential in lymphoblasts or whole blood cells; however, a diagnostic assay for a bipolar disorder according to the invention can also employ changes in membrane potential in lymphocytes, erythrocytes, as well as in other cells.

In additional embodiments, $Na^+K^+$ ATPase activity and therefore membrane potential is manipulated by incubating cells in $K^+$-free buffer and/or with one or more compounds that alter the $Na^+$ and $K^+$ ionic gradients in the cells. Comparisons between cells from bipolar patients and control cells from unaffected individuals (negative controls) incubated under corresponding conditions reveal significant differences that can be quantified and used to diagnose a bipolar disorder. Likewise, comparisons between cells from bipolar patients and cells from other individuals known to have a bipolar disorder (positive controls) incubated under corresponding conditions reveal a lack of a significant difference that can be used to diagnose a bipolar disorder.

Unipolar disorder may be diagnosed in a similar manner. For example, comparisons between cells from unipolar patients and control cells from unaffected individuals (negative controls) incubated under corresponding conditions reveal significant differences that can be quantified and used to diagnose unipolar disorder. Likewise, comparisons between cells from unipolar patients and cells from other individuals known to have unipolar disorder incubated under corresponding conditions reveal a lack of a significant difference that can be used to diagnose unipolar disorder.

In a preferred embodiment, a diagnostic assay for unipolar disorder according to the invention utilizes changes in membrane potential in whole blood cells; however, a diagnostic assay for unipolar disorder can also employ changes in membrane potential in lymphoblasts, lymphocytes, erythrocytes, as well as in other cells.

The membrane potential of a patient's cells can be ascertained by any conventional method, such as by measuring the fluorescence intensity of a lipophilic fluorescent dye. For example, membrane potentials may be measured using 3,3'-dihexyloxacarbocyanine iodide $DiOC_6(3)$, a cell-permeant, voltage sensitive, green-fluorescent dye, in conjunction with a fluorescence spectrometer.

DETAILED DESCRIPTION OF THE INVENTION

Figure 1:
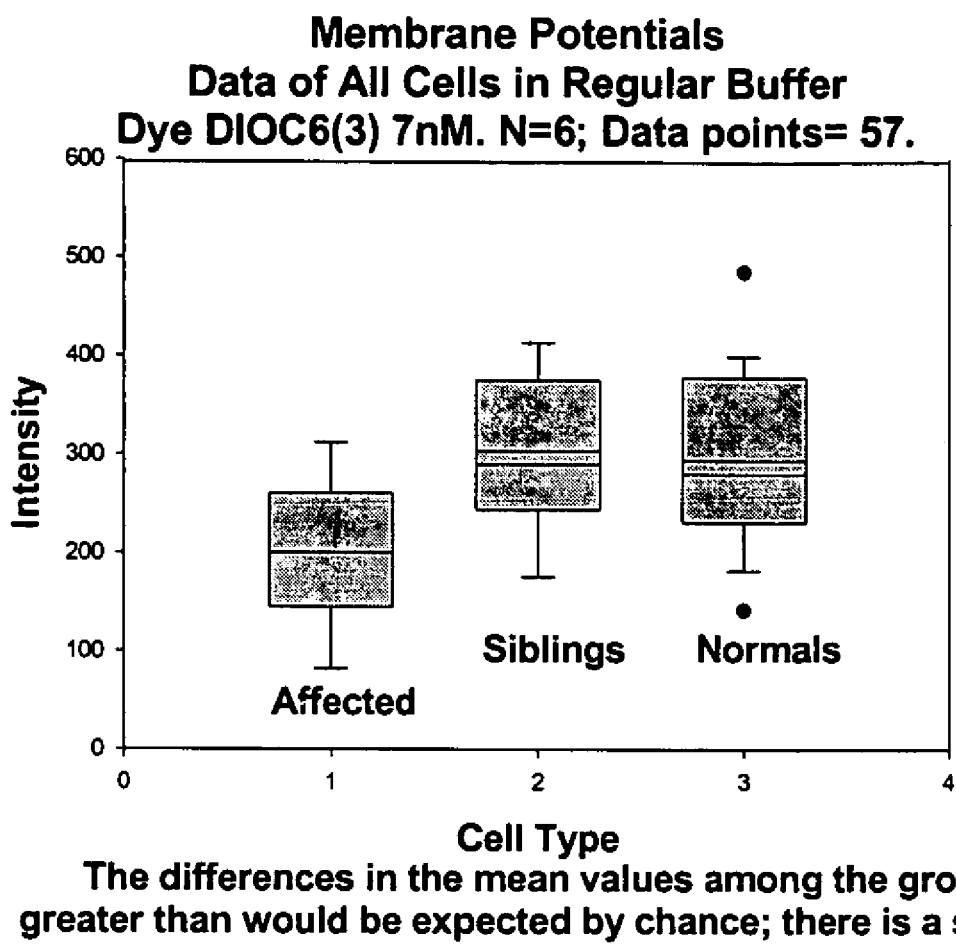
FIG. 1 shows the membrane potentials of affected (bipolar I) lymphoblasts, non-affected sibling lymphoblasts, and normal lymphoblasts, as indicated by fluorescence intensity of $DiOC_6(3)$ (7 nM), in regular buffer containing $K^+$.

The present invention provides a method for diagnosing a patient with a bipolar disorder by comparing the membrane potential of cells of the patient with corresponding control cells of one or more people known not to have a bipolar disorder (negative controls) and/or corresponding bipolar control cells of one or more people known to have a bipolar disorder (positive controls). In experiments described herein, the membrane potentials of lymphoblasts and whole blood cells are ascertained and compared. However, a diagnostic assay according to the present invention can utilize any cell type, such as, but not limited to, erythrocytes, platelets, leukocytes, macrophages, monocytes, dendritic cells, fibroblasts, epidermal cells, mucosal tissue cells, cells in the cerebrospinal fluid, hair cells, etc. Cells present in blood, skin cells, hair cells, or mucosal tissue cells may be more convenient to use because of the ease of harvesting these cell types.

For purposes of a diagnostic assay for a bipolar disorder disclosed herein, "corresponding control cells" means that the cells of the patient are the same type of cells as the control cells of the people known to not have a bipolar disorder. Similarly, for purposes of a diagnostic assay for unipolar disorder disclosed herein, "corresponding control cells" means that the cells of the patient are the same type of cells as the control cells of the people known to not have unipolar disorder. For example, if the cells of the patient are lymphoblasts, the "corresponding control cells" are lymphoblasts. Likewise, if the cells of the patient are whole blood cells, the "corresponding control cells" are whole blood cells.

For purposes of a diagnostic assay for a bipolar disorder disclosed herein, "corresponding bipolar control cells" means that the cells of the patient are the same type of cells as the bipolar control cells of the people known to have a bipolar disorder. For example, if the cells of the patient are lymphoblasts, the "corresponding bipolar control cells" are lymphoblasts. Likewise, if the cells of the patient are whole blood cells, the "corresponding bipolar control cells" are whole blood cells.

For purposes of a diagnostic assay for unipolar disorder disclosed herein, "corresponding unipolar control cells" means that the cells of the patient are the same type of cells as the unipolar control cells of the people known to have unipolar disorder. For example, if the cells of the patient are whole blood cells, the "corresponding unipolar control cells" are whole blood cells. Likewise, if the cells of the patient are lymphoblasts, the "corresponding unipolar control cells" are lymphoblasts.

In a preferred embodiment, a diagnostic assay according to the present invention involves manipulating the membrane potential in cells by either incubating cells with a compound that alters ATPase activity and/or by incubating cells in potassium-free media. The membrane potential of the cells is then ascertained following such treatment.

As indicated above, a cell's membrane potential is the result of the different concentration of ions on either side of the membrane. The activity of the $Na^+K^+$ ATPase pump, which regulates the concentration of $Na^+$ and $K^+$ to maintain homeostasis, can be altered by a variety of external stimuli, including various chemicals. When the $Na^+$ and $K^+$ ionic gradients are modulated by some means, the cell regulates the activity of the $Na^+K^+$ ATPase in an effort to return the ionic gradients to normal levels. Some compounds, such as ethacrynate, monensin, and monensin decyl ester, alter the activity of the $Na^+K^+$ ATPase by increasing the intracellular levels of sodium. Other compounds, such as phorbol 12-myristate 13-acetate (PMA), 12-O-tetradecanoylphorbol 13-acetate, phorbol 12-myristate 13-acetate 4-O-methyl ether, phorbol 12,13-dibutyrate (PDBu), phorbol 12,13-didecanoate (PDD), phorbol 12,13-dinonanoate 20-homovanillate, and other phorbol esters alter the activity of the Na$^+$K$^+$ ATPase by increasing the density of the Na$^+$K$^+$ ATPase on the cell surface. Thus, the activity of the Na$^+$K$^+$ ATPase is affected by its structure, its density, and compounds (both endogenous and exogenous) that affect the structure and density. Genes may play a role also.

Table 1 below shows other examples of compounds that alter the activity of the Na$^+$K$^+$ ATPase, either indirectly by altering the K$^+$ and/or Na$^+$ ionic gradients or by acting on the Na$^+$K$^+$ ATPase itself.

TABLE 1

| Chemical | K$^+$ | Na$^+$ | K$^+$ & Na$^+$ | Na$^+$K$^+$ ATPase |
|---|---|---|---|---|
| Valinomycin | X | | | |
| Monensin | | X | | |
| Gramicidin | | X | | |
| PCMBS | | X | | |
| Veratridine | | X | | |
| Ethacrynate | | | X | |
| PMA | | | | X |
| Dopamine | | | | X |
| Catacholamines | | | | X |
| Phorbol Esters | | | | X |
| Ouabain | | | | X |
| Lithium | X | X | X | X |
| Valproate | | | | X |
| Lamotrigine | | | | X |
| Cocaine | | | X | |
| Nicotine | | X | | |
| R0-31-8220 | | | | X |
| Oxymetazoline | | | | X |
| Calcineurin | | | | X |
| Topiramate | | | | X |
| Peptide Hormones | | | | X |
| Sorbitol | | | | X |
| Diuretics | | | X | |

In several embodiments, an assay according to the present invention employs such Na$^+$K$^+$ ATPase-altering compounds to help diagnose patients with a bipolar disorder. In other embodiments, an assay according to the present invention employs such Na$^+$K$^+$ ATPase-altering compounds to help diagnose patients with unipolar disorder.

The compounds that are described herein are merely examples of the compounds that could be used to alter Na$^+$K$^+$ ATPase activity. For example, any compound that increases the density and/or activity of the Na$^+$K$^+$ ATPase can be used in a diagnostic assay according to the present invention.

In another embodiment, a compound that decreases the density and/or activity of the Na$^+$ K$^+$ ATPase may be used in a diagnostic assay according to the present invention. For example, low concentrations of ouabain may be useful in differentiating bipolar cells from normal cells.

Thus, for purposes of this disclosure, "alters Na$^+$K$^+$ ATPase activity" includes directly altering Na$^+$K$^+$ ATPase activity by acting directly upon the Na$^+$K$^+$ ATPase as well as indirectly altering Na$^+$K$^+$ ATPase activity by, for example, increasing the intracellular sodium concentration. Furthermore, "alters Na$^+$K$^+$ ATPase activity" includes increasing or decreasing Na$^+$K$^+$ ATPase activity, although increasing Na$^+$K$^+$ ATPase activity is preferred.

Potassium uptake in cells of bipolar patients is significantly reduced compared to potassium uptake in cells of normal, unaffected patients. In several embodiments of the present invention, the membrane potential of cells incubated in potassium-free buffer is ascertained with or without incubation with compounds that alter the activity of the Na$^+$K$^+$ ATPase.

Examples of buffers that may be used in a diagnostic assay according to the present invention, along with their useful pH ranges, are shown in Table 2 below.

TABLE 2

| Composition | Lower pH | Upper pH |
|---|---|---|
| Glycyl-glycine-piperazine-2HCl—NaOH | 4.4 | 10.8 |
| MES-NaOH—NaCl | 5.2 | 7.1 |
| TRIS-malic acid-NaOH | 5.2 | 8.6 |
| MES-NaOH | 5.6 | 6.8 |
| ADA-NaOH—NaCl | 5.6 | 7.5 |
| ACES-NaOH—NaCl | 5.9 | 7.8 |
| ACES-NaOH—NaCl | 5.9 | 7.8 |
| BES-NaOH—NaCl | 6.2 | 8.1 |
| MOPS-NaOH—NaCl | 6.25 | 8.15 |
| TES-NaOH—NaCl | 6.55 | 8.45 |
| MOPS-KOH | 6.6 | 7.8 |
| HEPES-NaOH—NaCl | 6.6 | 8.5 |
| TRIS-HCl | 7.0 | 9.0 |
| HEPPSO-NaOH | 7.4 | 8.4 |
| BICINE-NaOH—NaCl | 7.4 | 9.3 |
| TAPS-NaOH—NaCl | 7.45 | 9.35 |
| HEPPS (EPPS)-NaOH | 7.5 | 8.7 |
| TRICINE-NaOH | 7.6 | 8.6 |
| BICINE-NaOH | 7.7 | 8.9 |

Potassium-containing buffers that may be used in a diagnostic assay according to the present invention can be created by adding potassium to the buffers shown in the table above that do not contain potassium. Potassium-containing buffers useful in a diagnostic assay according to the present preferably have a K$^+$ concentration in the range of approximately 2 mM to 7 mM, more preferably have a K$^+$ concentration of approximately 5 mM, and still more preferably have a K$^+$ concentration of 5 mM.

The K$^+$-containing buffer used in the examples set forth below is a HEPES buffer to which potassium has also been added (5 mM KCl, 4 mM NaHCO$_3$, 5 mM HEPES, 134 mM NaCl, 2.3 mM CaCl$_2$, and 5 mM glucose; pH 7.3-7.5, preferably 7.4), and is also referred to as "regular" or "stock" buffer. The K$^+$-free buffer used in the examples is a HEPES buffer without potassium (4 mM NaHCO$_3$, 5 mM HEPES, 134 mM NaCl, 2.3 mM CaCl$_2$, and 5 mM glucose; pH 6.6-7.0, preferably 6.8).

The membrane potential of a patient's cells may be ascertained by any conventional method, such as by examining the fluorescence intensity of a potential-sensitive lipophilic fluorescent dye. The membrane potential is directly proportional to the intensity of fluorescence according to the following equation: $I=CV$, wherein I is the fluorescence intensity of a lipophilic fluorescent dye, V is the voltage or membrane potential, and C is a constant that can vary depending on a number of factors such as, but not limited to, temperature, lamp intensity, number of cells, concentration of the fluorescent dye, incubation time, and lipid composition of cells used. The calibration and determination of the value for C can be a cumbersome and unreliable procedure. Thus, according to the present invention, by using the ratio of the fluorescence intensity (Il) of one sample of cells to the fluorescence intensity (I2) of another sample of cells, the constant (C) is canceled out. Such ratio-metric measurements are preferred over absolute measurements.

Examples of potential-sensitive dyes that may be adapted for use in a diagnostic assay according to the present invention, along with their charges and optical responses, are shown below in Table 3 (all available from Molecular Probes Inc., Eugene, Oreg., US).

TABLE 3

| Dye | Structure (Charge) | Optical Response |
|---|---|---|
| DiOC$_2$(3) | Carbocyanine | Slow; fluorescence |
| DiOC$_5$(3) | (cationic) | response to |
| DiOC$_6$(3) | | depolarization depends on |
| DiSC$_3$(5) | | staining concentration |
| DiIC$_1$(5) | | and detection method. |
| JC-1 | Carbocyanine | Slow; fluorescence |
| JC-9 | (cationic) | emission ratio 585/520 nm increases upon membrane hyperpolarization. |
| Tetramethyl-rhodamine methyl and ethyl esters Rhodamine 123 | Rhodamine (cationic) | Slow; used to obtain unbiased images of potential-dependent dye distribution. |
| Oxonol V | Oxonol | Slow; fluorescence |
| Oxonol VI | (anionic) | decreases upon membrane hyperpolarization. |
| DiBAC$_4$(3) | Oxonol | Slow; fluorescence |
| DiBAC$_4$(5) | (anionic) | decreases upon membrane |
| DiSBAC$_2$(3) | | hyperpolarization. |
| Merocyanine 540 | Merocyanine | Fast/Slow (biphasic response). |

Indo-(DiI), thia-(DiS) and oxa-(DiO) carbocyanines with short alkyl tails (<7 carbon atoms) were among the first potentiometric fluorescent probes developed. These cationic dyes accumulate on hyperpolarized membranes and are translocated into the lipid bilayer. DiOC$_6$(3) (3,3'-dihexyloxacarbocyanine iodide), a cell-permeant, voltage sensitive, green-fluorescent dye, has been the most widely used carbocyanine dye for membrane potential measurements, followed closely by DiOC$_5$(3). Thus, in a preferred embodiment of a diagnostic assay according to the present invention, membrane potentials may be measured using DiOC$_6$(3) in conjunction with a fluorescence spectrometer.

One embodiment of the present invention involves a direct comparison of membrane potentials between cells of a patient in need of a bipolar disorder diagnosis and control cells. See, e.g., Example 2 and FIG. 2. In particular, this embodiment provides a method for diagnosing a bipolar disorder in a patient, comprising:

(a) ascertaining the mean membrane potential of cells of the patient; and one or both of the following steps (b) and (c):

(b) comparing the mean membrane potential of the cells of the patient with the mean membrane potential of corresponding control cells of one or more people known to not have said bipolar disorder, wherein a significant difference between the mean membrane potential of the cells of the patient and the mean membrane potential of corresponding control cells indicates that the patient has said bipolar disorder;

(c) comparing the mean membrane potential of the cells of the patient with the mean membrane potential of corresponding bipolar control cells of one or more people known to have said bipolar disorder, wherein the lack of a significant difference between the mean membrane potential of the cells of the patient and the mean membrane potential of the corresponding bipolar control cells indicates that the patient has said bipolar disorder.

In one embodiment, steps (a) and (b) are performed. In another embodiment, steps (a) and (c) are performed. In another embodiment, steps (a), (b) and (c) are performed.

A preferred embodiment of the present invention involves a comparison of the ratios of membrane potentials in K$^+$-free buffer to those in K$^+$-containing buffer. See, for example, Example 3 and FIG. 4. In particular, this embodiment provides a method for diagnosing a bipolar disorder in a patient, comprising:

(a) obtaining a patient ratio of (i) the mean membrane potential of cells of the patient incubated in the absence of K$^+$ to (ii) the mean membrane potential of cells of the patient incubated in the presence of K$^+$; and one or both of the following steps (b) and (c):

(b) comparing the patient ratio obtained in (a) to a control ratio, wherein the control ratio is the ratio of (iii) the mean membrane potential of corresponding control cells of one or more people known to not have said bipolar disorder incubated in the absence of K$^+$ to (iv) the mean membrane potential of corresponding control cells of one or more people known to not have said bipolar disorder incubated in the presence of K$^+$, wherein a significant difference between the patient ratio compared to the control ratio indicates that the patient has said bipolar disorder;

(c) comparing the patient ratio obtained in (a) to a bipolar control ratio, wherein the bipolar control ratio is the ratio of (v) the mean membrane potential of corresponding bipolar control cells of one or more people known to have said bipolar disorder incubated in the absence of K$^+$ to (vi) the mean membrane potential of corresponding bipolar control cells of one or more people known to have said bipolar disorder incubated in the presence of K$^+$, wherein the lack of a significant difference between the patient ratio and the bipolar control ratio indicates that the patient has said bipolar disorder.

In one embodiment, steps (a) and (b) are performed. In another embodiment, steps (a) and (c) are performed. In another embodiment, steps (a), (b) and (c) are performed.

In a preferred embodiment, the significant difference between the patient ratio compared to the control ratio is that the patient ratio is significantly higher than the control ratio.

These comparative ratios, wherein the patient ratio is compared to the control ratio and/or the bipolar control ratio, can be illustrated as follows:

Patient Ratio $$\frac{\text{(i) mean membrane potential of cells of the patient incubated in the absence of K}^+}{\text{(ii) mean membrane potential of cells of the patient incubated in the presence of K}^+}$$

compared to:

Control Ratio $$\frac{\text{(iii) mean membrane potential of corresponding control cells incubated in the absence of K}^+}{\text{(iv) mean membrane potential of corresponding control cells incubated in the presence of K}^+}$$

and/or compared to:

Bipolar Control Ratio $$\frac{\text{(v) mean membrane potential of corresponding bipolar control cells incubated in the absence of } K^+}{\text{(vi) mean membrane potential of corresponding bipolar control cells incubated in the presence of } K^+.}$$

According to the above, when $K^+$ is present, it is preferably present at a concentration of approximately 2-7 mM, more preferably at a concentration of approximately 5 mM, and still more preferably at a concentration of 5 mM.

In another embodiment, the cells of the patient are incubated in the presence of a compound that alters $Na^+K^+$ ATPase activity; and the corresponding control cells, the corresponding bipolar control cells, or both the corresponding control cells and the corresponding bipolar control cells are also incubated in the presence of the compound that alters $Na^+K^+$ ATPase activity.

Yet another preferred embodiment of the present invention involves a comparison of the ratio of membrane potential with and without a $Na^+K^+$ ATPase-altering compound. See, e.g., Example 5 and FIG. 8, and Example 10 and FIG. 15. In particular, this embodiment provides a method for diagnosing a bipolar disorder in a patient, comprising:

(a) obtaining a patient ratio of (i) the mean membrane potential of cells of the patient incubated in the presence of a compound that alters $Na^+K^+$ ATPase activity to (ii) the mean membrane potential of cells of the patient incubated in the absence of the compound that alters $Na^+K^+$ ATPase activity; and one or both of the following steps (b) and (c):

(b) comparing the patient ratio obtained in (a) to a control ratio, wherein the control ratio is the ratio of (iii) the mean membrane potential of corresponding control cells of one or more people known to not have said bipolar disorder incubated in the presence of a compound that alters $Na^+K^+$ ATPase activity to (iv) the mean membrane potential of corresponding control cells of one or more people known to not have said bipolar disorder incubated in the absence of the compound that alters $Na^+K^+$ ATPase activity, wherein a significantly lower patient ratio compared to the control ratio indicates that the patient has said bipolar disorder;

(c) comparing the patient ratio obtained in (a) to a bipolar control ratio, wherein the bipolar control ratio is the ratio of (v) the mean membrane potential of corresponding bipolar control cells of one or more people known to have said bipolar disorder incubated in the presence of a compound that alters $Na^+K^+$ ATPase activity to (vi) the mean membrane potential of corresponding bipolar control cells of one or more people known to have said bipolar disorder incubated in the absence of the compound that alters $Na^+K^+$ ATPase activity, wherein the lack of a significant difference between the patient ratio compared to the bipolar control ratio indicates that the patient has said bipolar disorder.

In one embodiment, steps (a) and (b) are performed. In another embodiment, steps (a) and (c) are performed. In another embodiment, steps (a), (b) and (c) are performed.

These comparative ratios, wherein the patient ratio is compared to the control ratio and/or the bipolar control ratio, can be illustrated as follows:

Patient Ratio $$\frac{\text{(i) mean membrane potential of cells of the patient incubated in the presence of a compound that alters } Na^+K^+ \textit{ ATPase} \text{ activity}}{\text{(ii) mean membrane potential of cells of the patient incubated in the absence of the compound that alters } Na^+K^+ \textit{ ATPase} \text{ activity}}$$

compared to:

Control Ratio $$\frac{\text{(iii) mean membrane potential of corresponding control cells incubated in the presence of a compound that alters } Na^+K^+ \textit{ ATPase} \text{ activity}}{\text{(iv) mean membrane potential of corresponding control cells incubated in the absence of the compound that alters } Na^+K^+ \textit{ ATPase} \text{ activity}}$$

and/or compared to:

Bipolar Control Ratio $$\frac{\text{(v) mean membrane potential of corresponding bipolar control cells incubated in the presence of a compound that alters } Na^+K^+ \textit{ ATPase} \text{ activity}}{\text{(vi) mean membrane potential of corresponding bipolar control cells incubated in the absence of the compound that alters } Na^+K^+ \textit{ ATPase} \text{ activity}.}$$

In one embodiment, the cells are incubated in the presence of $K^+$, wherein the $K^+$ concentration is preferably approximately 2-7 mM, more preferably approximately 5 mM, and still more preferably 5 mM. In another embodiment, the cells are incubated in the absence of $K^+$. Preferably, the cells incubated in the presence of a compound that alters $Na^+K^+$ ATPase activity are incubated in the absence of $K^+$, and the cells incubated in the absence of the compound that alters $Na^+K^+$ ATPase activity are incubated in the presence of $K^+$.

Still another preferred embodiment of the present invention involves a comparison of the relative ratios of membrane potentials in $K^+$-free buffer to those in $K^+$-containing buffer with and without a $Na^+K^+$ ATPase-altering compound. See, e.g., Examples 4 and 7 and FIGS. 5 and 11. In particular, this embodiment provides a method for diagnosing a bipolar disorder in a patient, comprising:

(a) obtaining a ratio (patient ratio I) of (i) the mean membrane potential of cells of the patient incubated in the absence of $K^+$ and in the presence of a compound that alters $Na^+K^+$ ATPase activity to (ii) the mean membrane potential of cells of the patient incubated in the absence of $K^+$ and in the absence of the compound that alters $Na^+K^+$ ATPase activity;

(b) obtaining a ratio (patient ratio II) of (iii) the mean membrane potential of cells of the patient incubated in the presence of $K^+$ and in the presence of the compound that alters $Na^+K^+$ ATPase activity to (iv) the mean membrane potential of cells of the patient incubated in the presence of K$^+$ and in the absence of the compound that alters Na$^+$K$^+$ ATPase activity;

(c) obtaining a relative ratio (Relative Patient Ratio) of patient ratio I to patient ratio II; and one or both of the following steps (d) and (e):

(d) comparing the Relative Patient Ratio to a Relative Control Ratio, wherein the Relative Control Ratio is the relative ratio of control ratio I to control ratio II, wherein control ratio I is the ratio of (i') the mean membrane potential of corresponding control cells of one or more people known to not have said bipolar disorder incubated in the absence of K$^+$ and in the presence of a compound that alters Na$^+$K$^+$ ATPase activity to (ii') the mean membrane potential of corresponding control cells of one or more people known to not have said bipolar disorder incubated in the absence of K$^+$ and in the absence of the compound that alters Na$^+$K$^+$ ATPase activity, and wherein control ratio II is the ratio of (iii') the mean membrane potential of corresponding control cells of one or more people known to not have said bipolar disorder incubated in the presence of K$^+$ and in the presence of the compound that alters Na$^+$K$^+$ ATPase activity to (iv') the mean membrane potential of corresponding control cells of one or more people known to not have said bipolar disorder incubated in the presence of K$^+$ and in the absence of the compound that alters Na$^+$K$^+$ ATPase activity, wherein a significant difference between the Relative Patient Ratio compared to the Relative Control Ratio indicates that the patient has said bipolar disorder;

(e) comparing the Relative Patient Ratio to a Relative Bipolar Control Ratio, wherein the Relative Bipolar Control Ratio is the relative ratio of bipolar control ratio I to bipolar control ratio II, wherein bipolar control ratio I is the ratio of (i") the mean membrane potential of corresponding bipolar control cells of one or more people known to have said bipolar disorder incubated in the absence of K$^+$ and in the presence of a compound that alters Na$^+$K$^+$ ATPase activity to (ii") the mean membrane potential of corresponding bipolar control cells of one or more people known to have said bipolar disorder incubated in the absence of K$^+$ and in the absence of the compound that alters Na$^+$K$^+$ ATPase activity, and wherein bipolar control ratio II is the ratio of (iii") the mean membrane potential of corresponding bipolar control cells of one or more people known to have said bipolar disorder incubated in the presence of K$^+$ and in the presence of the compound that alters Na$^+$K$^+$ ATPase activity to (iv") the mean membrane potential of corresponding bipolar control cells of one or more people known to have said bipolar disorder incubated in the presence of K$^+$ and in the absence of the compound that alters Na$^+$K$^+$ ATPase activity, wherein the lack of a significant difference between the Relative Patient Ratio compared to the Relative Bipolar Control Ratio indicates that the patient has bipolar disorder.

In one embodiment, steps (a), (b), (c), and (d) are performed. In another embodiment, steps (a), (b), (c), and (e) are performed. In another embodiment, steps (a), (b), (c), (d), and (e) are performed.

In a preferred embodiment, the significant difference between the Relative Patient Ratio and the Relative Control Ratio is that the Relative Patient Ratio is significantly higher than the Relative Control Ratio.

These comparative ratios, wherein the Relative Patient Ratio is compared to the Relative Control Ratio and/or the Relative Bipolar Control Ratio, can be illustrated as follows:

Relative Patient Ratio

Patient Ratio I $$\frac{\text{(i) mean membrane potential of cells of the patient incubated in the absence of K}^+ \text{ and in the presence of a compound that alters Na}^+\text{K}^+ \text{ ATPase activity}}{\text{(ii) mean membrane potential of cells of the patient incubated in the absence of K}^+ \text{ and in the absence of the compound that alters Na}^+\text{K}^+ \text{ ATPase activity}}$$

Patient Ratio II $$\frac{\text{(iii) mean membrane potential of cells of the patient incubated in the presence of K}^+ \text{ and in the presence of the compound that alters Na}^+\text{K}^+ \text{ ATPase activity}}{\text{(iv) mean membrane potential of cells of the patient incubated in the presence of K}^+ \text{ and in the absence of the compound that alters Na}^+\text{K}^+ \text{ ATPase activity}}$$

compared to:

Relative Control Ratio

Control Ratio I $$\frac{(i')\text{ mean membrane potential of corresponding control cells incubated in the absence of K}^+ \text{ and in the presence of a compound that alters Na}^+\text{K}^+ \text{ ATPase activity}}{(ii')\text{ mean membrane potential of corresponding control cells incubated in the absence of K}^+ \text{ and in the absence of the compound that alters Na}^+\text{K}^+ \text{ ATPase activity}}$$

Control Ratio II $$\frac{(iii')\text{ mean membrane potential of corresponding control cells incubated in the presence of K}^+ \text{ and in the presence of the compound that alters Na}^+\text{K}^+ \text{ ATPase activity}}{(iv')\text{ mean membrane potential of corresponding control cells incubated in the presence of } K^+ \text{ and in the absence of the compound that alters Na}^+\text{K}^+ \text{ ATPase activity}}$$

and/or compared to:

Relative Bipolar Control Ratio

Bipolar Control Ratio I $$\frac{(i'')\text{ mean membrane potential of corresponding bipolar control cells incubated in the absence of } K^+ \text{ and in the presence of a compound that alters Na}^+K^+ \text{ ATPase activity}}{(ii'')\text{ mean membrane potential of corresponding bipolar control cells incubated in the absence of } K^+ \text{ and in the absence of the compound that alters Na}^+K^+ \text{ ATPase activity}}$$

Bipolar Control Ratio II $$\frac{(iii'')\text{ mean membrane potential of corresponding bipolar control cells incubated in the presence of } K^+ \text{ and in the presence of the compound that alters Na}^+K^+ \text{ ATPase activity}}{(iv'')\text{ mean membrane potential of corresponding bipolar control cells incubated in the presence of } K^+ \text{ and in the absence of the compound that alters Na}^+K^+ \text{ ATPase activity}}$$

Yet another embodiment of the present invention involves a comparison of the repolarization rate between cells of a patient being diagnosed and control cells. See, e.g., Example 4 and FIG. 7. In particular, this embodiment provides a method for diagnosing a bipolar disorder in a patient, comprising:

(a) ascertaining a mean rate of repolarization in cells of the patient incubated in the presence of a compound that alters Na$^+$K$^+$ ATPase activity; and one or both of the following steps (b) and (c):

(b) comparing the mean rate of repolarization ascertained in (a) to the mean rate of repolarization in corresponding control cells of one or more people known to not have said bipolar disorder incubated in the presence of the compound that alters Na$^+$K$^+$ ATPase activity, wherein a significant difference between the mean rate of repolarization in the cells of the patient compared to the mean rate of repolarization in the corresponding control cells indicates that the patient has said bipolar disorder;

(c) comparing the mean rate of repolarization ascertained in (a) to the mean rate of repolarization in corresponding bipolar control cells of one or more people known to have said bipolar disorder incubated in the presence of the compound that alters Na$^+$K$^+$ ATPase activity, wherein the lack of a significant difference between the mean rate of repolarization in the cells of the patient compared to the mean rate of repolarization in the corresponding bipolar control cells indicates that the patient has said bipolar disorder.

In one embodiment, steps (a) and (b) are performed. In another embodiment, steps (a) and (c) are performed. In another embodiment, steps (a), (b) and (c) are performed.

In a preferred embodiment, the significant difference between the mean rate of repolarization in the cells of the patient compared to the mean rate of repolarization in the corresponding control cells is that the mean rate of repolarization in the cells of the patient is significantly higher (e.g. P<0.05) than the mean rate of repolarization in the corresponding control cells.

In one embodiment, the cells are incubated in the presence of K$^+$. In another embodiment, the cells are incubated in the absence of K$^+$. As used herein, "presence of K$^+$" preferably means a K$^+$ concentration in the range of approximately 2 mM to 7 mM, preferably approximately 5 mM. For example, the K$^+$-containing HEPES buffer used in the examples below has a K$^+$ concentration of 5 mM.

In yet another embodiment, the present invention provides a method for diagnosing unipolar disorder in a patient, comprising:

(a) obtaining a patient ratio of (i) the mean membrane potential of cells of the patient incubated in the presence of a compound that alters Na$^+$K$^+$ ATPase activity to (ii) the mean membrane potential of cells of the patient incubated in the absence of the compound that alters Na$^+$K$^+$ ATPase activity; and one or both of the following steps (b) and (c):

(b) comparing the patient ratio obtained in (a) to a control ratio, wherein the control ratio is the ratio of (iii) the mean membrane potential of corresponding control cells of one or more people known to not have unipolar disorder incubated in the presence of a compound that alters Na$^+$K$^+$ ATPase activity to (iv) the mean membrane potential of corresponding control cells of one or more people known to not have unipolar disorder incubated in the absence of the compound that alters Na$^+$K$^+$ ATPase activity, wherein a significantly higher patient ratio compared to the control ratio indicates that the patient has unipolar disorder;

(c) comparing the patient ratio obtained in (a) to a unipolar control ratio, wherein the unipolar control ratio is the ratio of (v) the mean membrane potential of corresponding unipolar control cells of one or more people known to have unipolar disorder incubated in the presence of a compound that alters Na$^+$K$^+$ ATPase activity to (vi) the mean membrane potential of corresponding unipolar control cells of one or more people known to have unipolar disorder incubated in the absence of the compound that alters Na$^+$K$^+$ ATPase activity, wherein the lack of a significant difference between the patient ratio compared to the unipolar control ratio indicates that the patient has unipolar disorder.

In one embodiment, steps (a) and (b) are performed. In another embodiment, steps (a) and (c) are performed. In another embodiment, steps (a), (b) and (c) are performed.

These comparative ratios, wherein the patient ratio is compared to the control ratio and/or the unipolar control ratio, can be illustrated as follows:

Patient Ratio $$\frac{(i)\text{ mean membrane potential of cells of the patient incubated in the presence of a compound that alters Na}^+K^+ \text{ ATPase activity}}{(ii)\text{ mean membrane potential of cells of the patient incubated in the absence of the compound that alters Na}^+K^+ \text{ ATPase activity}}$$

compared to:

Control Ratio $$\frac{\text{(iii) mean membrane potential of corresponding control cells incubated in the presence of a compound that alters Na}^+\text{K}^+ \text{ATPase activity}}{\text{(iv) mean membrane potential of corresponding control cells incubated in the absence of the compound that alters Na}^+\text{K}^+ \text{ATPase activity}}$$

and/or compared to:

Unipolar Control Ratio $$\frac{\text{(v) mean membrane potential of corresponding unipolar control cells incubated in the presence of a compound that alters Na}^+\text{K}^+ \text{ATPase activity}}{\text{(vi) mean membrane potential of corresponding unipolar control cells incubated in the absence of the compound that alters Na}^+\text{K}^+ \text{ATPase activity.}}$$

In one embodiment, the cells are incubated in the presence of $K^+$, wherein the $K^+$ concentration is preferably approximately 2-7 mM, more preferably approximately 5 mM, and still more preferably 5 mM. In another embodiment, the cells are incubated in the absence of $K^+$. Preferably, the cells incubated in the presence of a compound that alters $Na^+K^+$ ATPase activity are incubated in the absence of $K^+$, and the cells incubated in the absence of the compound that alters $Na^+K^+$ ATPase activity are incubated in the presence of $K^+$.

In a preferred embodiment of a diagnostic assay for a bipolar disorder or unipolar disorder according to the present invention, the compound that alters $Na^+K^+$ ATPase activity is a compound selected from the group consisting of: valinomycin, monensin, gramicidin, p-chloromercurybenzenesulfonate (PCMBS), monensin decyl ester, veratridine, ethacrynate, dopamine, a catecholamine, a phorbol ester, ouabain, lithium, valproate, lamotrigine, cocaine, nicotine, the protein kinase C inhibitor R0—31-8220 (Wilkinson et al, *Biochem. J.* 294:335-337 (1993)), oxymetazoline, calcineurin, topiramate, a peptide hormone, sorbitol, and a diuretic. Preferably, the compound that alters $Na^+K^+$ ATPase activity increases $Na^+K^+$ ATPase activity.

In one embodiment of a diagnostic assay for a bipolar disorder or a diagnostic assay for unipolar disorder according to the present invention, the compound that alters $Na^+K^+$ ATPase activity is ethacrynate. Preferably, the concentration of ethacrynate is in the range of 1 μM to 100 μM, for example approximately 30 μM, more preferably 30 μM.

In another embodiment of a diagnostic assay for a bipolar disorder or a diagnostic assay for unipolar disorder according to the present invention, the compound that alters $Na^+K^+$ ATPase activity is monensin. Preferably, the concentration of monensin is in the range of 1 μM to 50 μM, for example approximately 10 μM, more preferably 10 μM.

In another embodiment of a diagnostic assay for a bipolar disorder or a diagnostic assay for unipolar disorder according to the present invention, the compound that alters $Na^+K^+$ ATPase activity is monensin decyl ester. Preferably, the concentration of monensin decyl ester is in the range of 1 μM to 50 μM, for example approximately 10 μM, more preferably 10 μM.

In another embodiment of a diagnostic assay for a bipolar disorder or a diagnostic assay for unipolar disorder according to the present invention, the compound that alters $Na^+K^+$ ATPase activity is a phorbol ester. Preferably, the phorbol ester is selected from the group consisting of: phorbol 12-myristate 13-acetate (PMA), 12-O-tetradecanoylphorbol 13-acetate, phorbol 12-myristate 13-acetate 4-O-methyl ether, phorbol 12,13-dibutyrate (PDBu), phorbol 12,13-didecanoate (PDD), and phorbol 12,13-dinonanoate 20-homovanillate. More preferably, the phorbol ester is phorbol 12-myristate 13-acetate (PMA). Preferably, the concentration of phorbol 12-myristate 13-acetate (PMA) is in the range of 0.1 μM to 10 μM, for example approximately 2 μM, more preferably 2 μM.

In another embodiment of a diagnostic assay for a bipolar disorder or a diagnostic assay for unipolar disorder according to the present invention, the compound that alters $Na^+K^+$ ATPase activity is lithium. Preferably, the concentration of lithium is in the range of 1 μM to 50 μM, for example approximately 20 mM, more preferably 20 mM.

In another preferred embodiment of a diagnostic assay for a bipolar disorder or a diagnostic assay for unipolar disorder according to the present invention, the mean membrane potential of the cells of the patient is determined by incubating the cells of the patient with a voltage-sensitive fluorescent dye and measuring the fluorescence intensity of the fluorescent dye. Preferably, the dye is a cell-permeant cationic dye. Preferably, the dye is a carbocyanine dye. In a preferred embodiment, the dye is 3,3'-dihexyloxacarbocyanine iodide $DiOC_6(3)$. Preferably, the concentration of dye is in the range of 1 nM to 500 nM, for example approximately 7 nM, more preferably 7 nM.

In another preferred embodiment of a diagnostic assay for a bipolar disorder or a diagnostic assay for unipolar disorder according to the present invention, the cells of the patient and the corresponding control cells (and corresponding bipolar and unipolar control cells, as appropriate) are selected from the group consisting of: lymphoblasts, erythrocytes, platelets, leukocytes, macrophages, monocytes, dendritic cells, fibroblasts, epidermal cells, mucosal tissue cells, cells in the cerebrospinal fluid, hair cells, and cells in whole blood. Preferably, the cells are lymphoblasts or cells in whole blood.

As described more fully in the examples below, the ratio of membrane potentials of bipolar cells in $K^+$-free buffer to membrane potentials of bipolar cells in $K^+$-containing buffer is significantly different from that of unaffected cells. Cells incubated in ethacrynate (30 μM) show significant differences between bipolar cells and unaffected cells. Cells incubated in monensin (10 μM) and in PMA (2 μM) also show significant differences in specific potentials. In addition to being a mood stabilizer, lithium serves as a medium to distinguish between bipolar cells and unaffected cells.

Further, as shown in a clinical trial using whole blood samples from bipolar, unipolar and schizophrenic patients described more fully below, the ratio of membrane potentials of bipolar cells is significantly different from that of matched control cells (P<0.001). In addition, the ratio of membrane potentials of unipolar cells is significantly different from that of matched control cells (P<0.001).

According to the present invention, when two sample groups are compared for differences for diagnostic purposes, e.g. affected cells and unaffected cells, student's t-test is preferably employed to determine if the two groups are significantly different from each other. As used herein, a "significant difference" (i.e., significantly higher or significantly lower) means that P<0.05. Commercially available statistical software is preferably used for this purpose.

According to the present invention, when more than two sample groups are compared to diagnose whether or not an individual patient is bipolar or unipolar, analysis of variance (ANOVA) test is preferably used. (See Beth Dawson and Robert G. Trapp, Basic and Clinical Biostatistics, Lange Medical Books, McGraw-Hill 3rd Edn.) In a preferred embodiment, an individual patient's cell sample is tested as described herein and six to twelve values are calculated. These patient values are treated as a first sample group and compared with a normal control group (negative control) and a bipolar group (positive control) as shown in Example 10. A bipolar diagnosis is made when there is a significant difference (P<0.05) between the normal control group (negative control) and the patient, but there is not a significant difference between the bipolar control group (positive control) and the patient. A similar procedure is used to determine whether or not a patient is unipolar.

Although the examples below describe experiments comparing membrane potentials of patients being diagnosed for a bipolar disorder to groups of controls that were examined contemporaneously, an assay according to the invention preferably compares the mean membrane potential of a patient's cells to predetermined control value or values. Thus, the standard control value(s) do not need to be determined contemporaneously with every patient assay for a bipolar disorder, but are preferably pre-determined for later comparisons with patients being diagnosed. Although not contemporaneous, assay conditions between patients and controls are preferably the same. Preferably, control data is pre-determined from various types of corresponding control cells, so that regardless of the type of cells from a patient being tested, control information already exists with which to make a comparison and thus a diagnosis. Furthermore, control data is preferably pre-determined using a control group known not to have any mental illness, in addition to control groups having mental illnesses such as a bipolar disorder, unipolar disorder, or schizophrenia.

The instant disclosure demonstrates that manipulation of $Na^+K^+$ ATPase activity provides an effective tool for differentiating bipolar cells from non-bipolar cells. Novel diagnostic assays for a bipolar disorder are thus provided. The instant disclosure also demonstrates that manipulation of $Na^+K^+$ ATPase activity is an effective tool for differentiating unipolar cells from non-unipolar cells, and therefore provides diagnostic assays for unipolar disorder. The specificity and sensitivity of the diagnostic assays described herein compare well with state-of-the-art diagnostic techniques for various other diseases.

The following examples are provided for illustrative purposes only and are in no way intended to limit the scope of the invention.

EXAMPLES

Example 1

Cell Cultures

Three groups of immortalized lymphoblast samples were obtained from the Human Genetic Mutant Cell Repository (Coriell Institute for Medical Research, Camden N.J.). The samples are shown in Table 4 below and included six from affected (bipolar I disorder) patients (A1 through A6), six from their siblings (S1 through S6), and six from unrelated normal control subjects matched by age and sex (N1 through N6).

TABLE 4

| Name | Coriell Number | Age | Sex |
|------|----------------|------|--------|
| A1 | GM09869 | 26 yr | Male |
| A2 | GM05977 | 22 yr | Female |
| A3 | GM05999 | 26 yr | Female |
| A4 | GM05918 | 16 yr | Female |
| A5 | GM06003 | 35 yr | Female |
| A6 | GM11051 | 25 yr | Female |
| S1 | GM05933 | 23 yr | Male |
| S2 | GM05914 | 28 yr | Female |
| S3 | GM05901 | 50 yr | Male |
| S4 | GM09215 | 18 yr | Male |
| S5 | GM05888 | 28 yr | Female |
| S6 | GM05901 | 55 yr | Female |
| N1 | GM05945 | 25 yr | Male |
| N2 | GM06160 | 28 yr | Female |
| N3 | GM05408 | 34 yr | Female |
| N4 | GM06862 | 26 yr | Female |
| N5 | GM06051 | 36 yr | Male |
| N6 | GM06861 | 36 yr | Male |

The cells were grown at 37° C. in RPMI 1640 culture medium (GIBCO, Life Technologies, Gaithersburg, Md., USA) with 15% fetal bovine serum and 1% penicillin.

Example 2

Determination of Membrane Potential

The membrane potentials of the bipolar I cells shown in Table 4 above (as well as in all other experiments, except where indicated) were measured using the following protocol. The cells cultured in the media described above were centrifuged at 210 g for 5 minutes at room temperature, then suspended in 3 ml of $K^+$-containing stock buffer (5 mM KCl, 4 mM $NaHCO_3$, 5 mM HEPES, 134 mM NaCl, 2.3 mM $CaCl_2$, and 5 mM glucose). The cells were counted and the desired number of cells were again suspended in the $K^+$-containing buffer. The membrane potentials were measured using 3,3'-dihexyloxacarbocyanine iodide $DiOC_6(3)$, a cell-permeant, voltage sensitive, green-fluorescent dye (Molecular Probes Inc. Eugene, Oreg. USA). The cells were preincubated for 30 minutes before measurements. The preincubated cell suspension was centrifuged at 210 g for 5 minutes and the cells were resuspended in the $K^+$-containing buffer without the dye in the buffer.

A fluorescence spectrometer (F2500 Hitachi, Japan) was used for the measurement of the membrane potential by measuring the fluorescence intensity of $DiOC_6(3)$, which is directly proportional to the membrane potential. The intensity of fluorescence was measured at an excitation wavelength of 488 nm and an output wavelength of 540 nm. The time of recordings varied from 10 seconds to 1500 seconds depending upon the experiment.

Membrane potential was expressed according to fluorescence intensity using the following equation: $I=CV$, wherein I is the fluorescence intensity of a lipophilic fluorescent dye $DiOC_6(3)$ being only one example of such a dye); V is the voltage or membrane potential; and C is a constant that can vary depending on a number of factors such as, but not limited to, temperature, lamp intensity, number of cells, concentration of the fluorescent dye, incubation time, and lipid composition of cells used. By using the ratio of the fluorescence intensity ($I_1$) of one sample of cells to the fluorescence intensity ($I_2$) of another sample of cells, the constant (C) could be canceled out The measurements of the fluorescence intensity (and thereby membrane potential, per the above equation) indicated that the mean membrane potential of the affected (bipolar I) cells was statistically distinguishable from that of the other cells. FIG. 1 shows box plots of the membrane potentials of lymphoblasts from the three groups tested, namely the affected (bipolar I) cells, non-affected sibling cells, and normal cells, as indicated by the fluorescence intensity of $DiOC_6$(3) (7 nM) in $K^+$-containing (regular) buffer. The differences in the mean values among the groups were greater than would be expected by chance. The mean fluorescence intensity of the affected (bipolar I) cells was significantly lower (P<0.001) by a one-way ANOVA test than that of the sibling cells as well as that of the normal control cells. There was no significant difference between normal cells and sibling cells. The box plots show the $5^{th}$, $25^{th}$, $50^{th}$, $75^{th}$, and $95^{th}$ percentile lines. The mean and median lines coincide for the affected cells, but are separated for the other two cell lines. Power of performed test with alpha=0.050:0.991. N=6. Data points=57.

Figure 2:
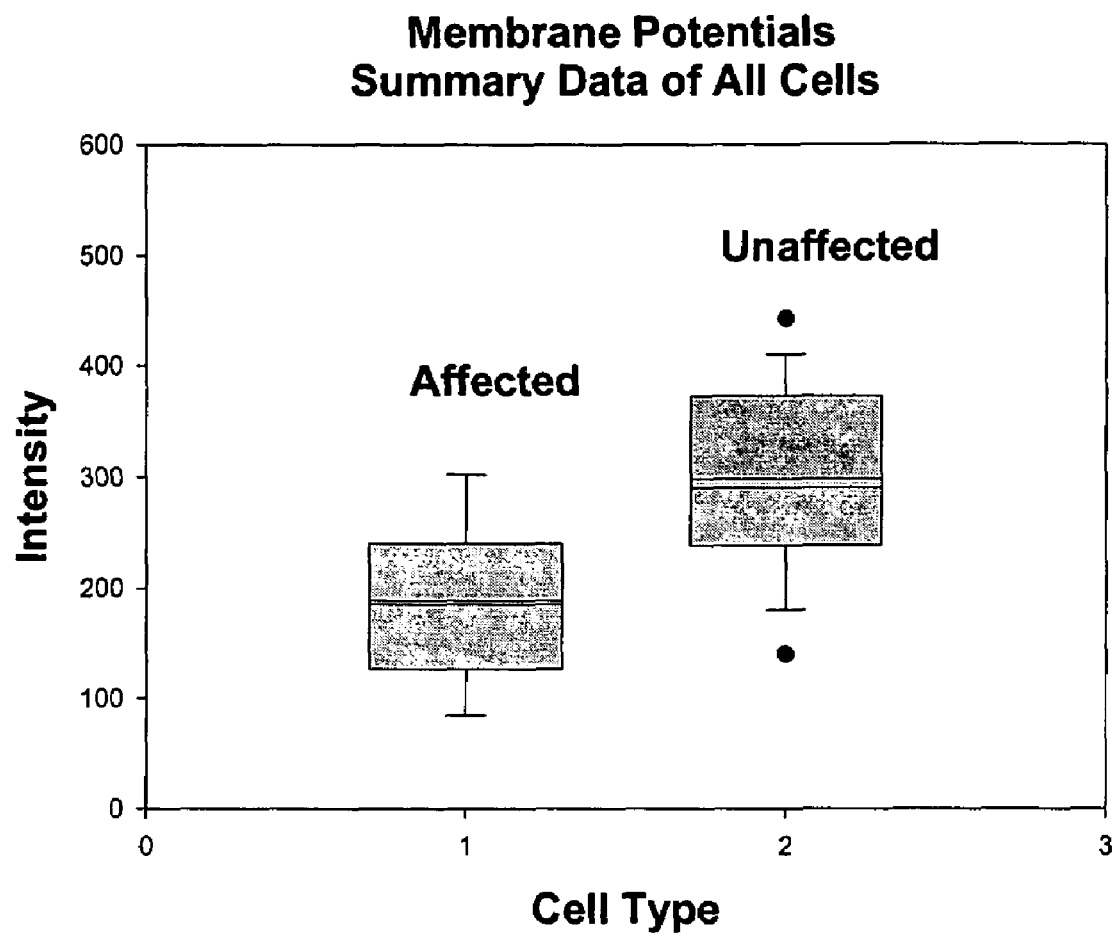
FIG. 2 shows the membrane potentials of affected (bipolar I) cells and unaffected cells, as indicated by the fluorescence intensity of $DiOC_6(3)$ in affected cells and the combination of non-affected sibling cells and normal cells.

A post-hoc comparison showed a significant difference between affected (bipolar I) cells vs. normal cells and sibling cells, but not between sibling cells and normal cells. Therefore sibling cells and normal cells were combined into a single, "unaffected" category. FIG. 2 shows the membrane potentials of affected (bipolar I) cells and unaffected cells, as indicated by the fluorescence intensity of $DiOC_6$(3) in affected cells and in the combination of non-affected sibling cells and normal cells. The difference in the mean values of the resulting two groups was greater than would be expected by chance. The mean fluorescence intensity of the affected (bipolar I) cells was significantly lower (P<0.001) than that of the unaffected cells. 95 percent confidence interval for difference of means: −159.577 to −66.090. Power of performed test with alpha=0.050:0.999.

Figure 3:
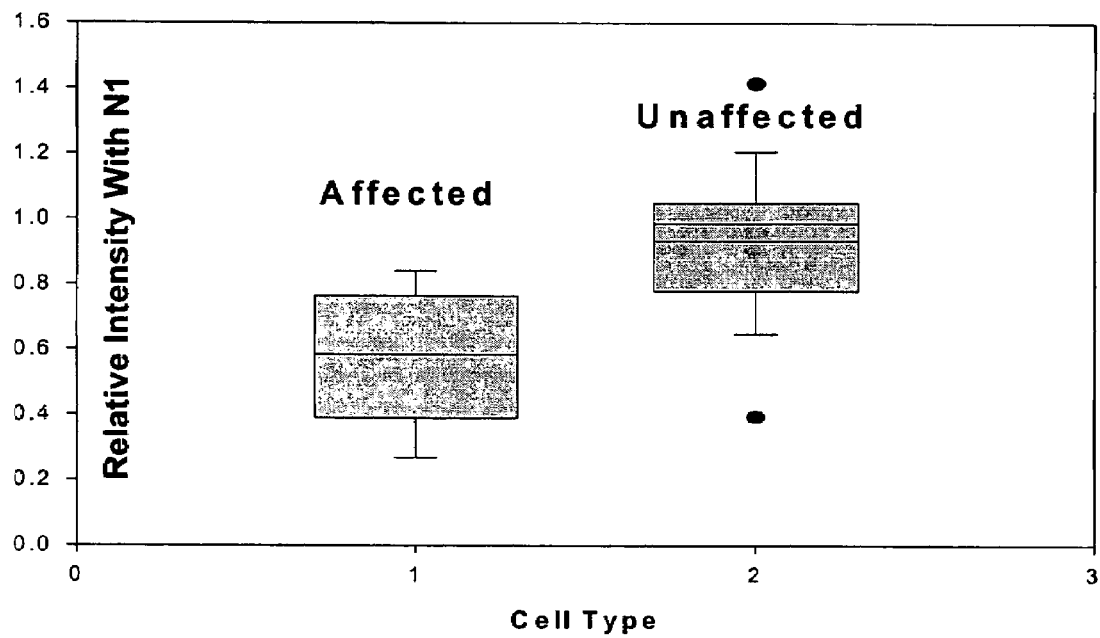
FIG. 3 shows the fluorescence intensity of $DiOC_6(3)$ in affected (bipolar I) cells and unaffected (sibling and normal) cells relative to the fluorescence intensity of $DiOC_6(3)$ in normal control cell N1.

An additional ratio-metric comparison was made by plotting a ratio of fluorescence intensities of the tested cells to that of a cell selected as a standard. FIG. 3 shows the fluorescence intensity of $DiOC_6$(3) in affected (bipolar I) cells and unaffected (sibling and normal) cells relative to the fluorescence intensity of $DiOC_6$(3) in the control cell, N1. This ratio-metric procedure accounted for variations in cell count and dye concentration. The difference in the mean values of the resulting two groups was greater than would be expected by chance. The mean relative intensity of the affected (bipolar I) cells was significantly lower (P<0.001) than that of the unaffected cells. t=−5.386 with 54 degrees of freedom. Power of performed test with alpha=0.050:1.000.

The data presented in this example and shown in FIGS. 1-3 indicates that the membrane potential of cells such as lymphoblasts can be used to distinguish groups of patients with bipolar I disorder from groups of unaffected controls.

Example 3

Membrane Potential In $K^+$-Free Buffer

Membrane potentials were also measured in $K^+$-free buffer to enable comparison with membrane potentials in $K^+$-containing buffer. As used herein, $K^+$-free buffer contains all of the components of the $K^+$-containing buffer, except potassium (4 mM $NaHCO_3$, 5 mM HEPES, 134 mM NaCl, 2.3 mM $CaCl_2$, and 5 mM glucose). Constant volumes of samples of each cell line were added to an equal volume of buffer containing an equal volume of dye. $K^+$-free buffer as well as $K^+$-containing buffer contained an equal volume of cells (and hence an equal number of cells from that culture sample) and an equal concentration of dye. Each variable was constant for each cell line in both buffers, so that the ratio of intensities was a true ratio-metric measurement.

Figure 4:
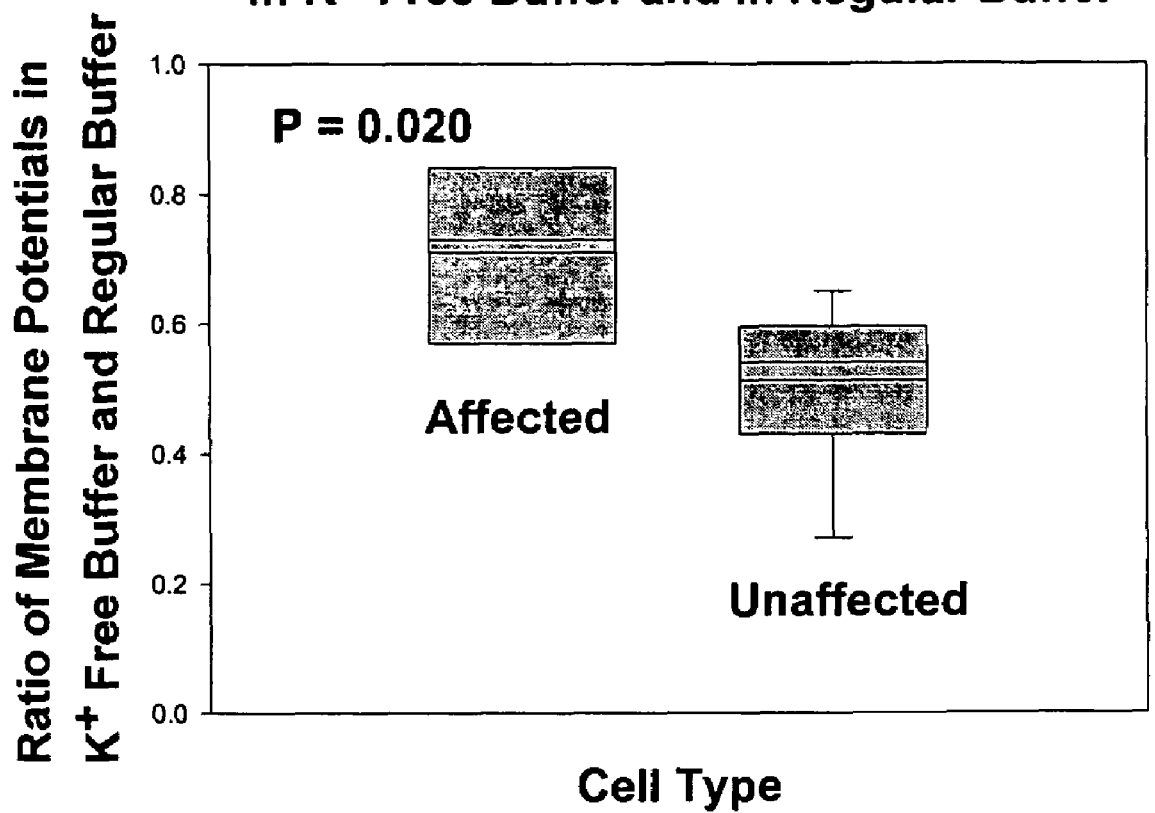
FIG. 4 shows a comparison of membrane potentials in $K^+$-free buffer and in buffer containing $K^+$, as indicated by the ratio of fluorescence intensity of $DiOC_6(3)$ in affected (bipolar I) cells and unaffected (sibling and normal) cells in $K^+$-free buffer and in $K^+$-containing (regular) buffer.

FIG. 4 shows a comparison of membrane potentials in $K^+$-free buffer with those in $K^+$-containing (regular) buffer, as indicated by fluorescence intensity. 70 nM $DiOC_6$(3) was added to the cells 30 minutes prior to measuring the membrane potential. The ratio of fluorescence intensity of $DiOC_6$(3) in $K^+$-free buffer to the fluorescence intensity of $DiOC_6$(3) in $K^+$-containing buffer was plotted in the y-axis. The mean value of the ratio of the membrane potential of affected cells was approximately 0.71. In comparison, the mean value of the ratio of the membrane potential of the unaffected cells was approximately 0.51. The ratio of the membrane potential of the unaffected cells was significantly lower than that in affected cells, as indicated by t-test (P=0.020).

The above procedure was also used for the ratio-metric measurements described below.

Example 4

Ethacrynate-Induced Changes in Membrane Potential

Ethacrynate is a loop diuretic prescribed for kidney patients that increases the intracellular sodium concentration and decreases the intracellular potassium concentration. When the intracellular sodium concentration increases, cells correspondingly regulate $Na^+K^+$ ATPase activity to pump the extra sodium out of the cells. Thus, these changes initiate the $Na^+K^+$ ATPase activity to normalize the ionic gradients.

The relative fluorescence intensity ratio of cells in $K^+$-free buffer was compared to that of cells in $K^+$-containing buffer with or without 30 μM ethacrynate. The cells were incubated with or without ethacrynate (30 μM) for 30 min in $K^+$-containing buffer or in $K^+$-free buffer. The membrane potential of these cells was determined by measuring the fluorescence intensity as described above. The intensity ratio (membrane potential with ethacrynate/membrane potential without ethacrynate) was compared to the intensity ratio in $K^+$-containing buffer and/or in $K^+$-free buffer. The relative intensity ratio was obtained by dividing the intensity ratio in $K^+$-free buffer by the intensity ratio in $K^+$-containing buffer.

A constant sample volume of each cell line was added to an equal volume of each buffer containing an equal volume of dye. Thus, the $K^+$-free buffer and the $K^+$-containing buffer contained an equal number of cells from each culture sample and an equal concentration of dye.

Figure 5:
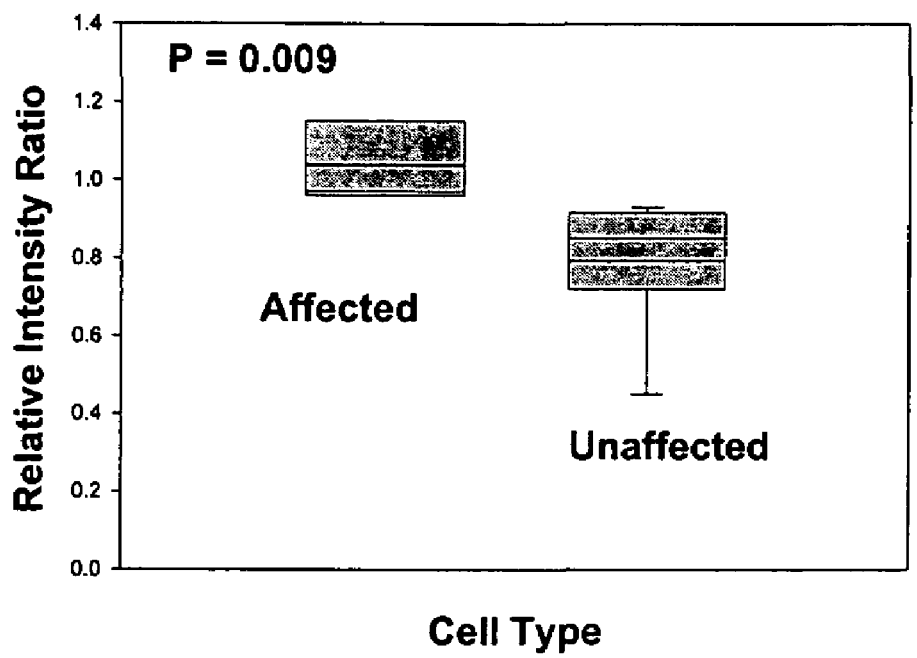
FIG. 5 shows ethacrynate-induced changes in membrane potential, as indicated by the relative ratio of the fluorescence intensity and therefore of the membrane potential of affected (bipolar I) cells and unaffected (sibling and normal) cells in $K^+$-free buffer and in $K^+$-containing (regular) buffer in the presence or absence of 30 µM ethacrynate.

As shown in FIG. 5, the relative intensity ratio of affected cells was significantly higher than that of unaffected cells by t-test. The mean value of the ratio of the fluorescence intensity of affected cells in $K^+$-free buffer to the fluorescence intensity of affected cells in $K^+$-containing (regular) buffer was approximately 1.04. The mean value of the ratio of fluorescent intensity of the unaffected cells in $K^+$-free buffer to the fluorescence intensity of unaffected cells in $K^+$-containing buffer was approximately 0.79. Further, the mean value of the ratio of the affected cells was statistically higher than the mean ratio of unaffected cells (P=0.009).

Figure 6:
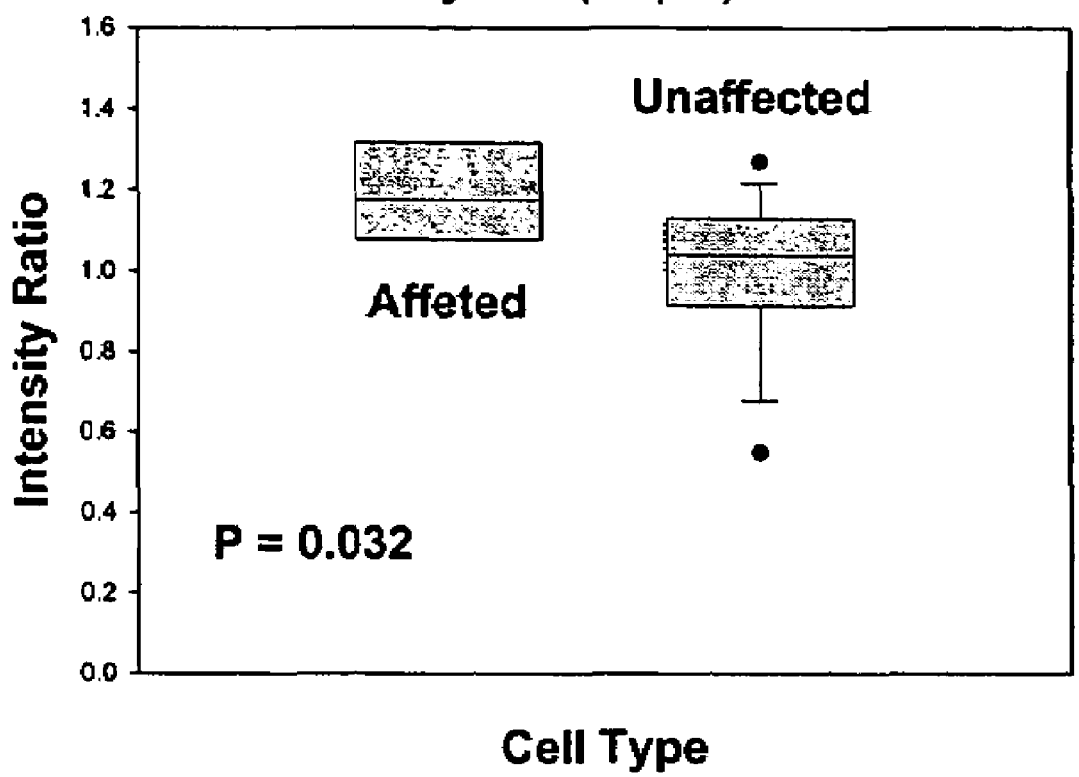
FIG. 6 shows the effect of ethacrynate on membrane potential, as indicated by the ratio of fluorescence intensity of affected (bipolar I) cells and unaffected (sibling and normal) cells in $K^+$-free buffer with or without the addition of 30 µM ethacrynate.

Similar differences were found in $K^+$-containing buffer alone or in $K^+$-free buffer alone. The fluorescence intensity of cells incubated in $K^+$-free buffer with 30 μM ethacrynate was compared to that of cells incubated in $K^+$-free buffer without ethacrynate. The membrane potential of these cells was determined by measuring the fluorescence intensity as described above. As shown in FIG. 6, the intensity ratio (membrane potential of cells incubated with ethacrynate/membrane potential of cells not incubated with ethacrynate) of affected cells was significantly higher than that of unaffected cells by t-test (P=0.032).

Figure 7:
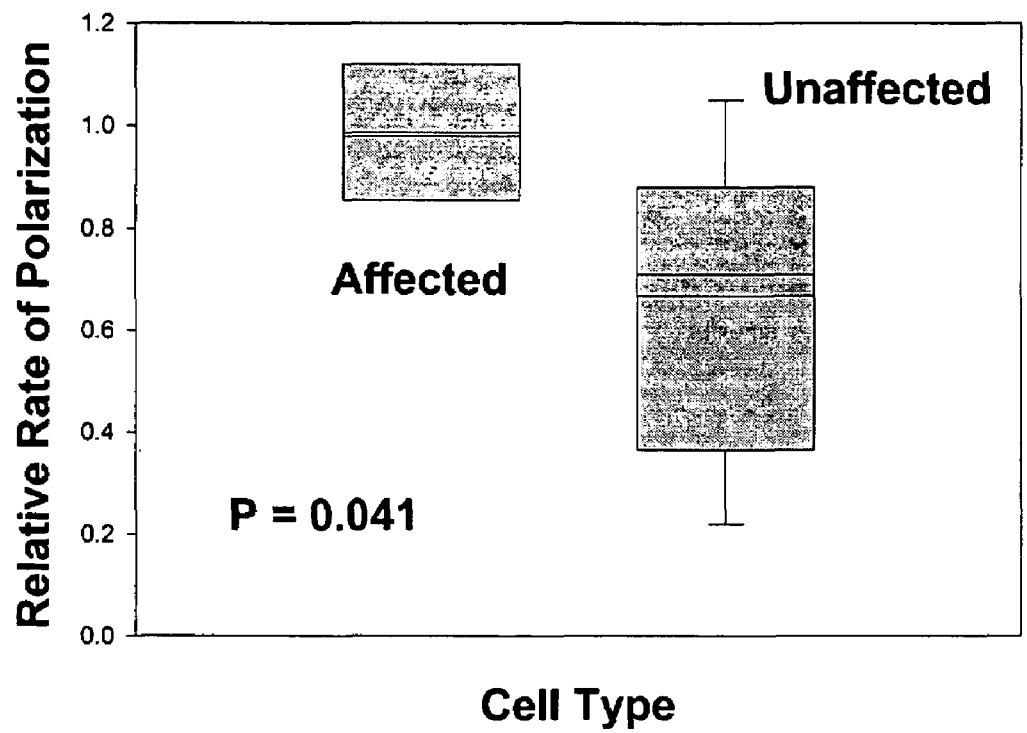
FIG. 7 shows the relative rate of polarization of affected (bipolar I) cells and unaffected (sibling and normal) cells incubated for 30 minutes in $K^+$-free buffer and in $K^+$-containing (regular) buffer in the presence or absence of 30 µM ethacrynate.

As the $Na^+K^+$ ATPase density on the cell surface increases, the intracellular sodium concentration decreases and the membrane potential begins to drop as a result of repolarization of the cell membrane. The rate of drop in membrane potential (repolarization rate) in affected cells incubated for 30 minutes in both $K^+$-free buffer and in $K^+$-containing (regular) buffer in the presence or absence of 30 µM ethacrynate was compared to that of unaffected cells incubated for 30 minutes in both $K^+$-free buffer and in $K^+$-containing buffer in the presence or absence of 30 µM ethacrynate. The difference in the median values between the two groups was greater than would be expected by chance. As shown in FIG. 7, the relative rate of repolarization was significantly higher in affected cells compared to that of unaffected cells (P=0.041, as determined by t-test).

Example 5

Monensin-Induced Changes in Membrane Potential

Monensin is an antibiotic ionophore having a 10-fold preference for $Na^+$ over $K^+$. Monensin increases the intracellular sodium concentration, thus changing the ratio of membrane potentials. The increase in sodium concentration in turn leads to an increase in $Na^+K^+$ ATPase density.

Figure 8:
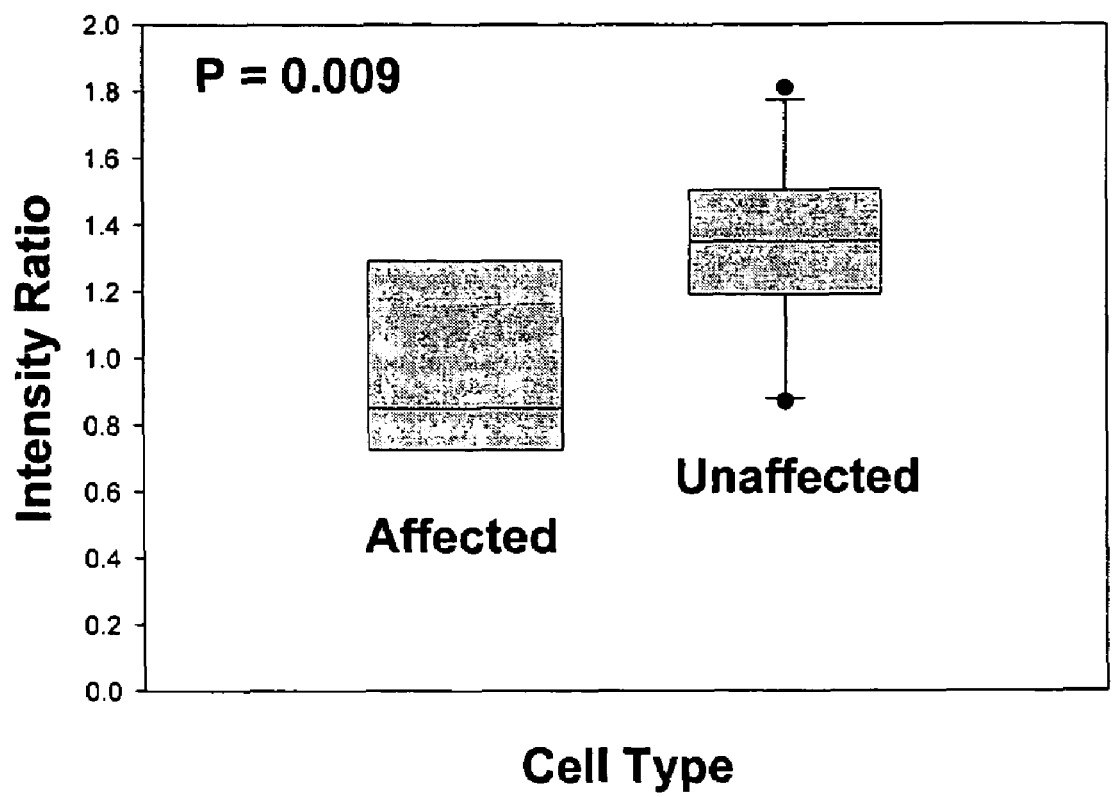
FIG. 8 shows the effect of monensin on membrane potential, as indicated by the ratio of fluorescence intensity of affected (bipolar I) cells and unaffected (sibling and normal) cells in $K^+$-free buffer with or without the addition of 10 µM monensin.

The fluorescence intensity of cells incubated in $K^+$-free buffer with 10 µM monensin was compared to that of cells incubated in $K^+$-free buffer without monensin. The cells were incubated for 30 minutes. The membrane potential of these cells was determined by measuring the fluorescence intensity as described above. As shown in FIG. 8, the intensity ratio (membrane potential of cells incubated with monensin/membrane potential of cells not incubated with monensin) of affected cells was significantly lower than that of unaffected cells by t-test (P=0.009).

Example 6

PMA-Induced Changes in Membrane Potential

Protein kinase C (PKC) is an essential enzyme involved in the phosphorylation of ATP, which provides energy for the $Na^+K^+$ ATPase. Furthermore, PKC activators such as PMA and inhibitors such as dopamine significantly alter $Na^+K^+$ ATPase density in the presence of monensin.

Figure 9:
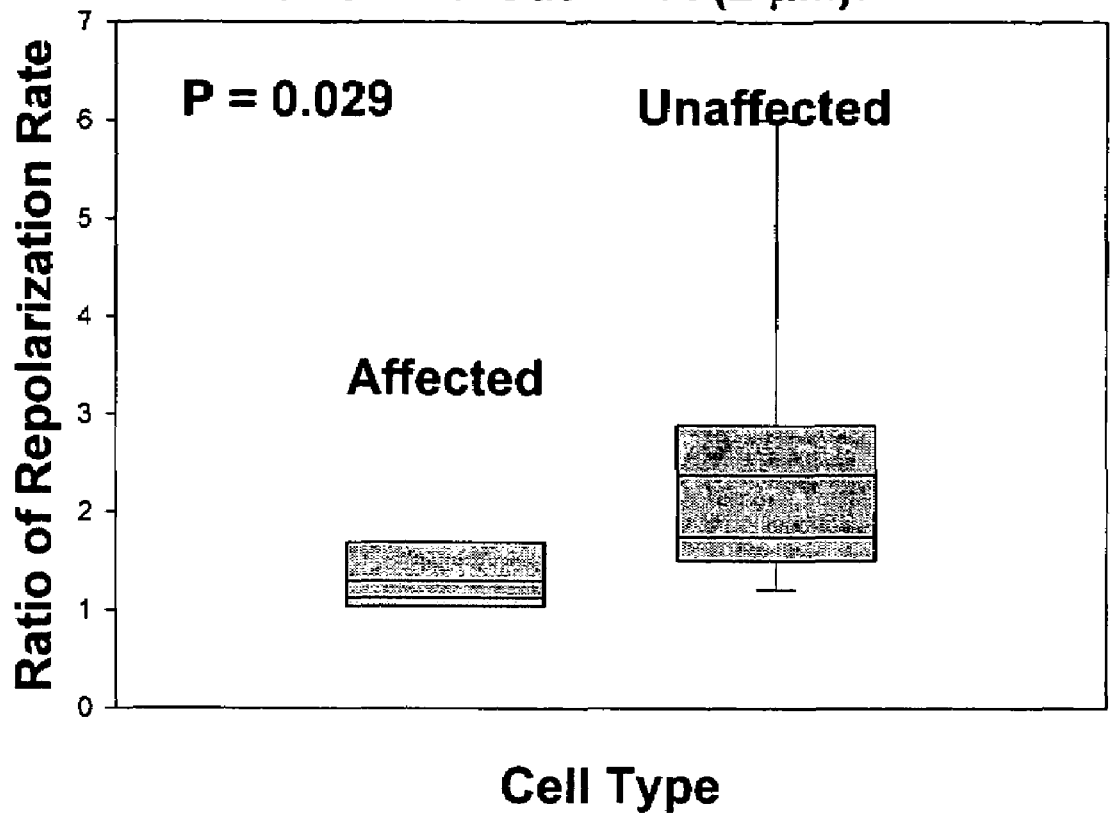
FIG. 9 shows the effect of phorbol 12-myristate 13-acetate (PMA) on the rate of repolarization, as indicated by the ratio of repolarization rate of affected (bipolar I) cells and unaffected (sibling and normal) cells in $K^+$-free buffer with or without 2 µM PMA.

The rate of drop in membrane potential after incubation with the protein kinase C (PKC) activator, phorbol 12-myristate 13-acetate (PMA), was compared in affected cells to that of unaffected cells. The membrane potential of these cells was determined by measuring the fluorescence intensity as described above. The rate of drop in membrane potential (repolarization rate) in affected cells was compared to that in unaffected cells in $K^+$-free buffer in the presence or absence of 2 µM PMA. The difference in the median values between the two groups was greater than would be expected by chance. The ratio of repolarization rate with PMA divided by the repolarization rate without PMA is shown in FIG. 9. FIG. 9 shows that when the cells were incubated in 2 µM PMA before membrane potential measurements, the repolarization rate in affected cells was significantly different from the repolarization rate in unaffected cells by t-test (P=0.029).

Figure 10:
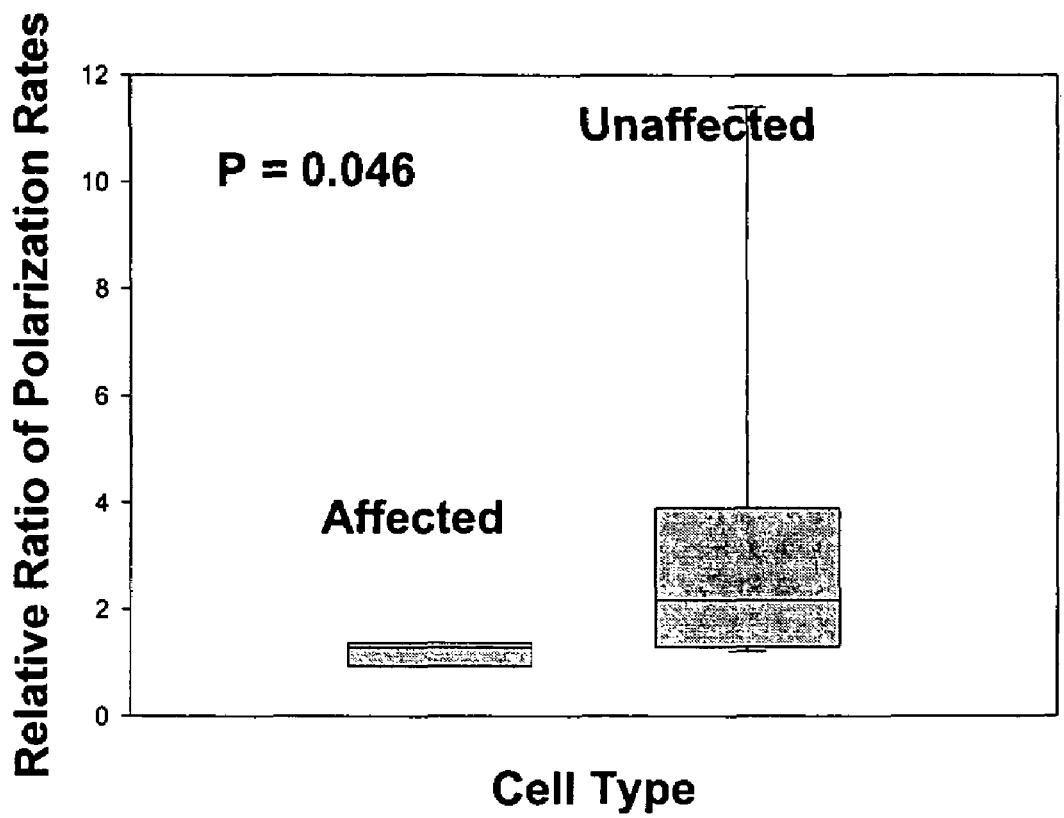
FIG. 10 shows the effect of PMA on the relative ratio of repolarization rates, as indicated by the ratio of repolarization rate of affected (bipolar I) cells and unaffected (sibling and normal) cells in both $K^+$-free buffer and in $K^+$-containing (regular) buffer with or without 2 µM PMA.

FIG. 10 shows the effect of PMA on the relative ratio of repolarization rates. The rate of drop in membrane potential (repolarization rate) in affected cells incubated for 30 minutes in both $K^+$-free buffer and in $K^+$-containing (regular) buffer in the presence or absence of 2 µM PMA was compared to that of unaffected cells incubated for 30 minutes in both $K^+$-free buffer and in $K^+$-containing buffer in the presence or absence of 2 µM PMA. The difference in the median values between the two groups was greater than would be expected by chance. As shown in FIG. 10, the relative ratio of repolarization rates was significantly lower in affected cells compared to than in unaffected cells (P=0.046, as determined by t-test).

Example 7

Lithium-Induced Changes in Membrane Potential

The effect of the addition of lithium, a clinically proven mood stabilizer, on changes in membrane potential in $K^+$-free buffer and in $K^+$-containing buffer was measured. Cells were incubated with or without lithium chloride (LiCl 20 mM) for 2 hours in $K^+$-free buffer or in $K^+$-containing buffer.

A constant sample volume of each cell line was added to an equal volume of each buffer containing an equal volume of dye. Thus, the $K^+$-free buffer and the $K^+$-containing buffer contained an equal number of cells from each culture sample and an equal concentration of dye.

Figure 11:
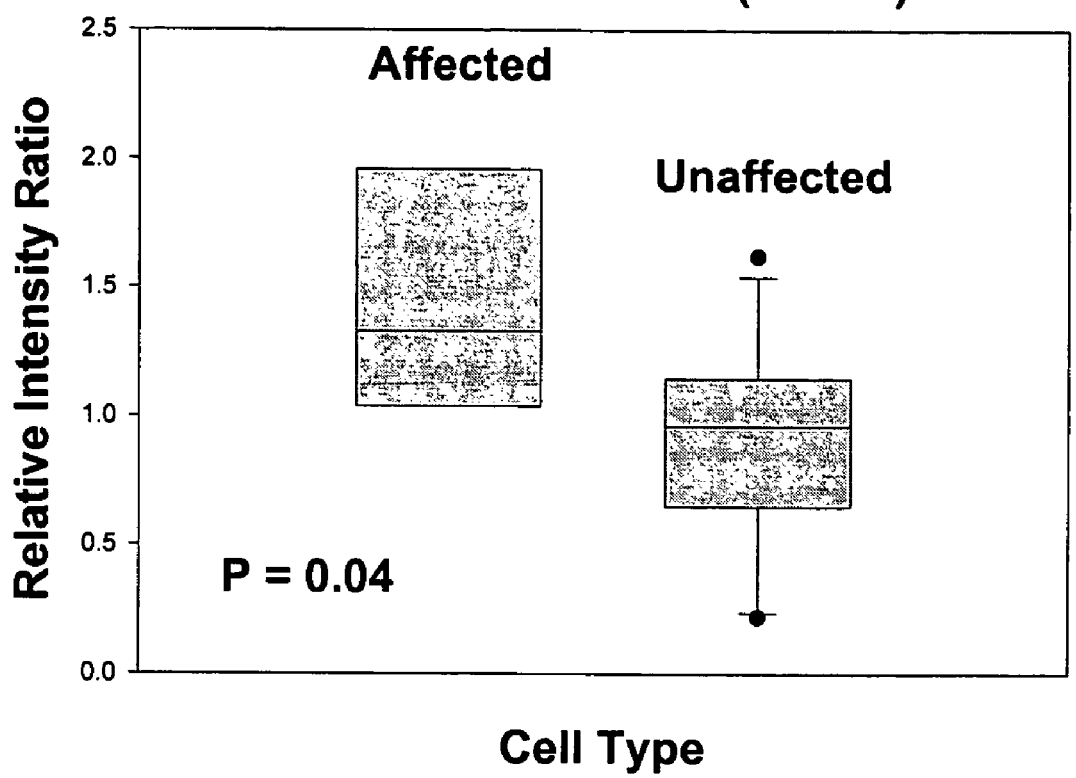
FIG. 11 shows the effect of lithium on membrane potential, as indicated by the relative ratio of the fluorescence intensity of affected (bipolar I) cells and unaffected (sibling and normal) cells in $K^+$-containing (regular) buffer and in $K^+$-free buffer in the presence or absence of 20 mM lithium chloride.

The membrane potential of these cells was determined by measuring the fluorescence intensity as described above. The intensity ratio (membrane potential with lithium/membrane potential without lithium) was compared to the intensity ratio in $K^+$-containing buffer and/or in $K^+$-free buffer. The relative intensity ratio was obtained by dividing the intensity ratio in $K^+$-free buffer by the intensity ratio in $K^+$-containing buffer. As shown in FIG. 11, the relative intensity ratio (ratio in $K^+$-free buffer with and without lithium/ratio in $K^+$-containing (regular) buffer with and without lithium) of affected cells was significantly higher than that of unaffected cells by t-test (P=0.04).

Example 8

Open Clinical Trials

A pilot clinical trial was conducted using blood samples from 12 clinically affected bipolar patients and 11 unaffected controls. The medical histories of the patients were known to the investigator measuring the membrane potentials; therefore, the trials described in this example were open trials. The patients ranged from 19 years to 77 years in age, and included males and females from different ethnic groups. Similarly, the controls ranged from 25 to 67 including males and females from different ethnic groups. The patients were all hospitalized following a confirmed manic episode. During the drawing of samples, all patients were on mood stabilizers, either lithium or valproate.

Because the volume of blood required to collect enough lymphocytes was beyond that permitted by the current protocol, the membrane potential of whole blood cells was determined. The volume of whole blood required was approximately 1 ml. The blood samples were kept on ice until they were stored at 4° C. All of the samples were tested within 48 hours.

Whole blood samples drawn from patients and controls were suspended in $K^+$-containing buffer without ethacrynate and in $K^+$-free buffer with 30 µM ethacrynate or with 100 mM sorbitol. The fluorescent dye $DiOC_6(3)$ was added to both suspensions and incubated for 30 minutes. The cell suspensions loaded with the dye were centrifuged, drained and resuspended in the respective buffers. The fluorescence intensity was measured for 10 seconds and the ratio of the intensity in $K^+$-free buffer to the intensity in $K^+$-containing buffer was calculated.

Tables 5 and 6 below present the statistical analysis of the data generated in the trials.

TABLE 5

Clinical Trials (Open Samples)
Normality Test: Passed (P > 0.050)
Equal Variance Test: Passed (P = 0.523)

| Group Name | N | Missing | Mean | Std Dev | SEM |
|---|---|---|---|---|---|
| Controls | 98 | 0 | 0.893 | 0.0485 | 0.00489 |
| Bipolars | 109 | 0 | 0.780 | 0.0521 | 0.00499 |

Difference 0.114
t = 16.204 with 205 degrees of freedom. (P = <0.001)
95 percent confidence interval for difference of means: 0.0999 to 0.128
The difference in the mean values of the two groups is greater than would be expected by chance; there is a statistically significant difference between the input groups (P = <0.001).
Power of performed test with alpha = 0.050: 1.000

TABLE 6

Descriptive Statistics:

| Column | Size | Missing | Mean | Std Dev | Std. Error | C.I. of Mean |
|---|---|---|---|---|---|---|
| Controls | 98 | 0 | 0.893 | 0.0485 | 0.00489 | 0.00971 |
| Bipolars | 109 | 0 | 0.780 | 0.0521 | 0.00499 | 0.00990 |

| Column | Range | Max | Min | Median | 25% | 75% |
|---|---|---|---|---|---|---|
| Controls | 0.256 | 1.053 | 0.797 | 0.893 | 0.860 | 0.925 |
| Bipolars | 0.250 | 0.880 | 0.629 | 0.778 | 0.751 | 0.817 |

| Column | Skewness | Kurtosis | K-S Dist. | K-S Prob. | Sum | Sum of Squares |
|---|---|---|---|---|---|---|
| Controls | 0.287 | 0.141 | 0.0418 | 0.863 | 87.558 | 78.457 |
| Bipolars | −0.425 | 0.0710 | 0.0693 | 0.219 | 84.988 | 66.559 |

Table 5 above indicates that these data passed both the normality test and equal variance test. Table 6 above shows that the mean value is very close to the median value for each of these groups, indicating that the data are normally distributed. The t-test shows significant variance (P<<0.001) among the two groups in open trials, with post-hoc comparisons showing significant differences between controls and bipolar patients.

Figure 12:
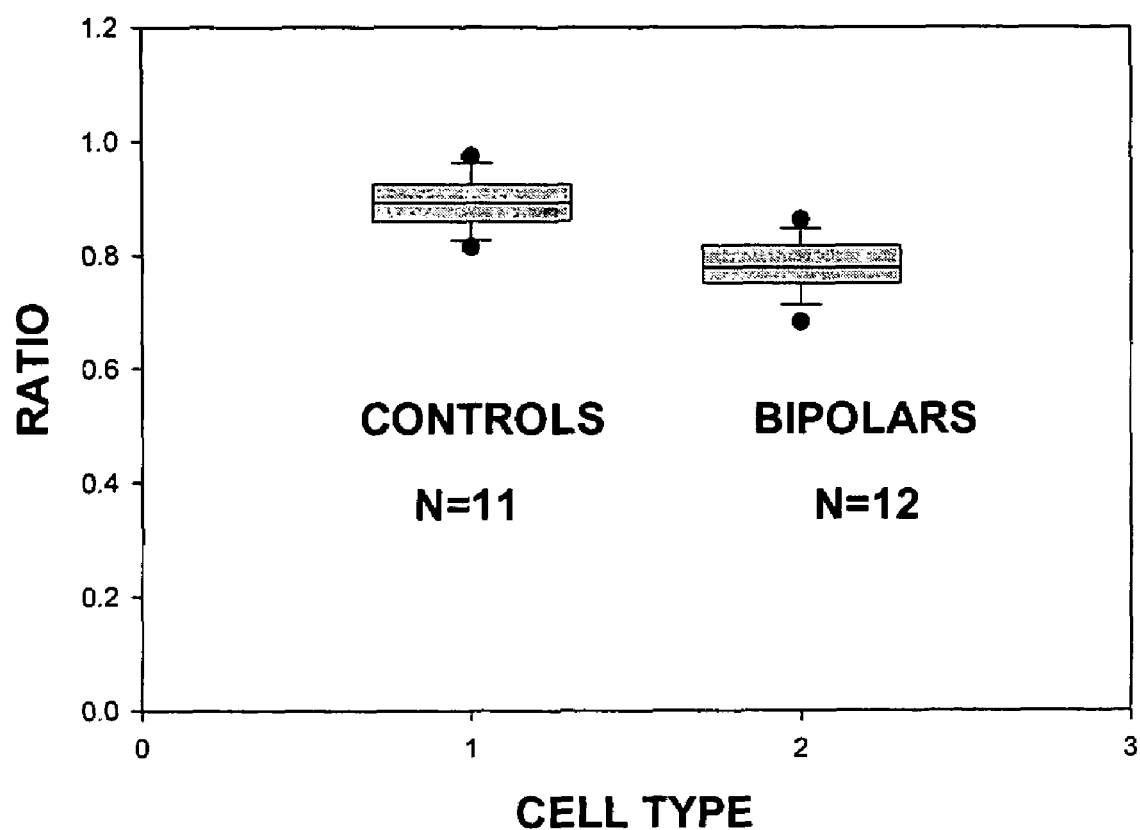
FIG. 12 shows the ratio of fluorescence intensities and therefore membrane potentials in $K^+$-free buffer containing 30 µM ethacrynate to the fluorescence intensity in $K^+$-containing buffer without ethacrynate in an open clinical trial using whole blood samples.

FIG. 12 graphically depicts the data presented in Tables 5 and 6 above, showing the ratio of fluorescence intensities of the control and bipolar groups in $K^+$-free buffer containing 30 μM ethacrynate to the fluorescence intensity in $K^+$-containing buffer without ethacrynate. The mean fluorescence intensity ratio of the bipolar samples was significantly lower than that of the control samples by t-test.

Figure 13:
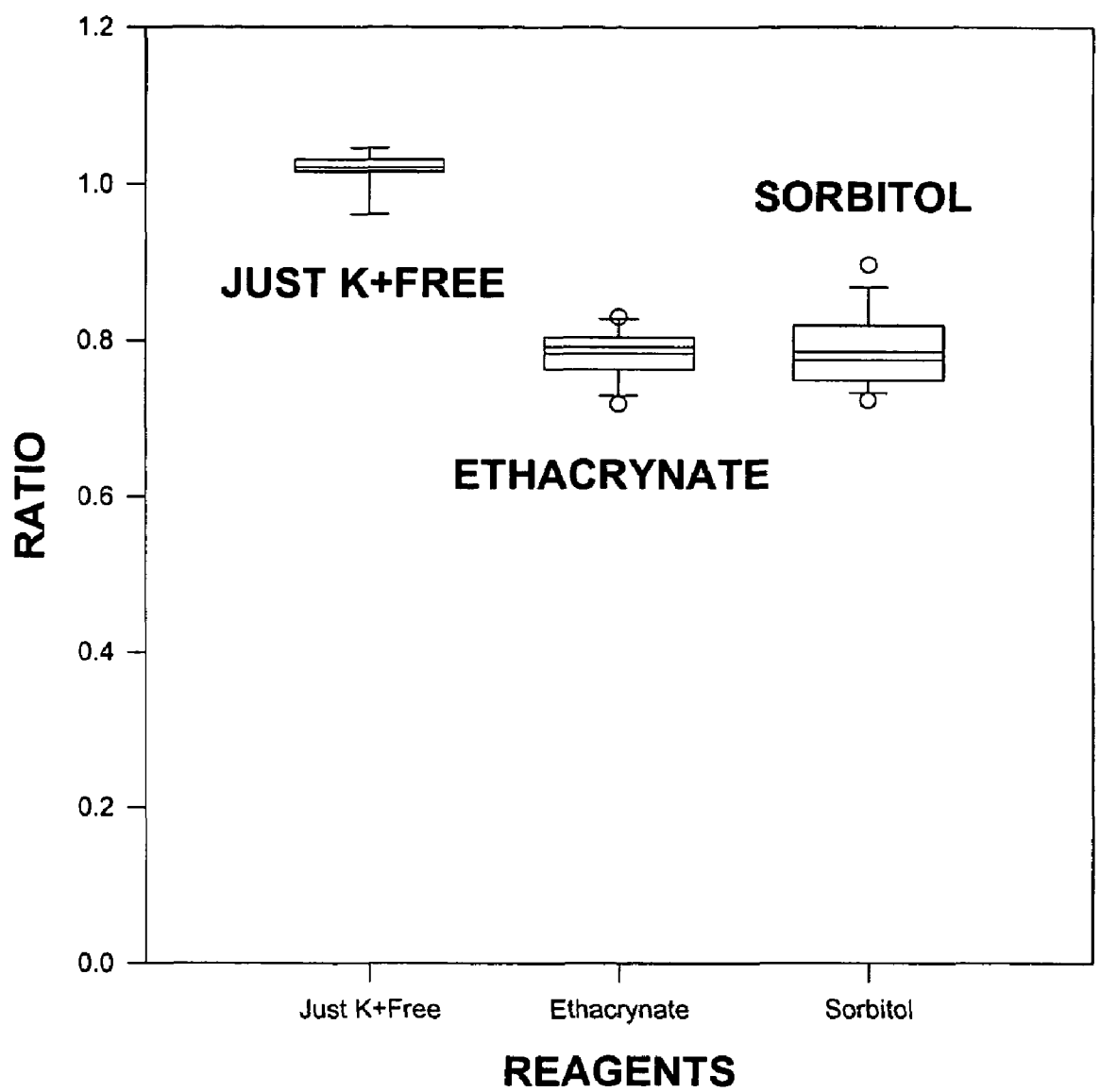
FIG. 13 shows a comparison of ethacrynate and sorbitol in $K^+$-free buffer, as used in the open clinical trial using whole blood samples.

FIG. 13 shows that with bipolar patients the results with sorbitol were comparable to the results with ethacrynate. This figure shows a comparison of fluorescence intensity ratios of bipolar cells using ethacrynate and sorbitol in $K^+$-free buffer.

Example 9

Blind Clinical Trials

A clinical trial was conducted using blood samples from the following four groups: schizophrenic, bipolar, and unipolar patients, as well as controls. The medical histories of these patients were unknown to the investigator measuring the membrane potentials; therefore, the trials described in this example were blind trials. The sample size was determined to be 5 with a power of 0.9, an alpha of 0.05, a difference in mean of 0.08, and a standard deviation of 0.03. However, more than 10 samples for each category were tested for a total sample size of 59. If a patient matched a diagnosis, structured clinical interviews according to DSM-IV guidelines were performed.

Whole blood samples drawn from patients and controls were suspended both in $K^+$-containing buffer and in $K^+$-free buffer with 30 μM ethacrynate or with 100 μM sorbitol. The fluorescent dye $DiOC_6(3)$ was added to both suspensions and incubated for 30 minutes. The cell suspensions loaded with the dye were centrifuged, drained and resuspended in the respective buffers. The fluorescence intensity was measured for 10 seconds and the ratio of the intensity in $K^+$-free buffer to the intensity in $K^+$-containing buffer was calculated.

Tables 7 and 8 below present the statistical analysis of the four groups.

TABLE 7

One Way Analysis of Variance SUMMARY OF BLIND TRIALS
Normality Test: Passed (P > 0.050)
Equal Variance Test: Failed (P = <0.001)
Test execution ended by user request, ANOVA on Ranks begun Kruskal-Wallis One Way Analysis of Variance on Ranks

| Group | N | Missing | Median | 25% | 75% |
|---|---|---|---|---|---|
| Controls | 173 | 0 | 0.850 | 0.829 | 0.869 |
| Schizophr. | 78 | 0 | 0.863 | 0.838 | 0.895 |
| Bipolars | 178 | 0 | 0.773 | 0.752 | 0.790 |
| Unipolars | 72 | 0 | 0.901 | 0.863 | 0.934 |

H = 351.025 with 3 degrees of freedom. (P = <0.001)
The differences in the median values among the treatment groups are greater than would be expected by chance; there is a statistically significant difference (P = <0.001)
To isolate the group or groups that differ from the others use a multiple comparison procedure.
All Pairwise Multiple Comparison Procedures (Dunn's Method):

| Comparison | Diff of Ranks | Q | P < 0.05 |
|---|---|---|---|
| Unipolars vs Bipolars | 308.546 | 15.260 | Yes |
| Unipolars vs Controls | 95.297 | 4.694 | Yes |
| Unipolars vs Schizophr. | 52.263 | 2.209 | No |
| Schizophr. vs Bipolars | 256.283 | 13.037 | Yes |
| Schizophr. vs Controls | 43.034 | 2.180 | No |
| Controls vs Bipolars | 213.249 | 13.797 | Yes |

TABLE 8

Descriptive Statistics: SUMMARY OF BLIND TESTS

| Column | Size | Missing | Mean | Std Dev | Std. Error | C.I. of Mean |
|---|---|---|---|---|---|---|
| Controls | 173 | 0 | 0.850 | 0.0290 | 0.00220 | 0.00435 |
| Schizophr. | 78 | 0 | 0.870 | 0.0428 | 0.00484 | 0.00964 |
| Bipolars | 178 | 0 | 0.768 | 0.0300 | 0.00225 | 0.00444 |
| Unipolars | 72 | 0 | 0.898 | 0.0486 | 0.00573 | 0.0114 |

| Column | Range | Max | Min | Median | 25% | 75% |
|---|---|---|---|---|---|---|

TABLE 8-continued

Descriptive Statistics: SUMMARY OF BLIND TESTS

| Controls | 0.180 | 0.929 | 0.749 | 0.850 | 0.829 | 0.869 |
| Schizophr. | 0.200 | 0.994 | 0.794 | 0.863 | 0.838 | 0.895 |
| Bipolars | 0.164 | 0.830 | 0.667 | 0.773 | 0.752 | 0.790 |
| Unipolars | 0.199 | 1.004 | 0.805 | 0.901 | 0.863 | 0.934 |

| Column | Skewness | Kurtosis | K-S Dist. | K-S Prob. | Sum | Sum of Squares |
|---|---|---|---|---|---|---|
| Controls | 0.0895 | 0.607 | 0.0400 | 0.661 | 147.073 | 125.176 |
| Schizophr. | 0.682 | 0.132 | 0.0827 | 0.203 | 67.885 | 59.222 |
| Bipolars | −0.601 | 0.187 | 0.0742 | 0.018 | 136.709 | 105.156 |
| Unipolars | 0.0506 | −0.849 | 0.0762 | 0.362 | 64.645 | 58.210 |

Figure 14:
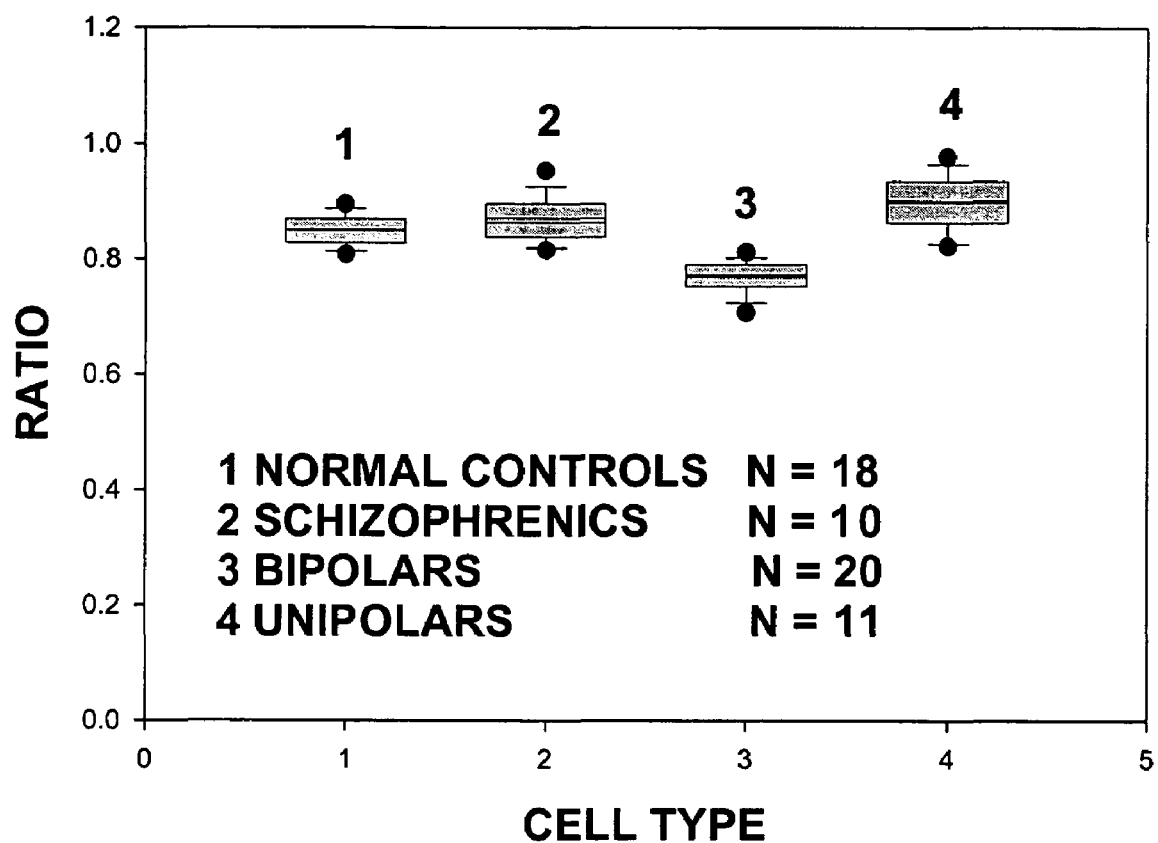
FIG. 14 shows the ratio of fluorescence intensities and therefore membrane potentials in $K^+$-free buffer containing 30 µM ethacrynate to the fluorescence intensity in $K^+$-containing buffer without ethacrynate in a blind clinical trial using whole blood samples from 18 normal controls, 10 schizophrenics, 11 unipolars, and 20 bipolars.

FIG. 14 graphically depicts the data presented in Tables 7 and 8 above, showing a summary of these blind test results using whole blood samples. The figure shows the ratio of fluorescence intensities of the sample groups in $K^+$-free buffer containing 30 μM ethacrynate to the fluorescence intensity in $K^+$-containing buffer without ethacrynate. The coefficient of variation ranged from 3.5 to 4.5 in all these tests. There were no significant differences among the normals and schizophrenics. However, blood samples from bipolar patients were significantly different from the other three groups, as determined by ANOVA ($P<<0.001$). In particular, the fluorescence intensity ratio of the bipolar samples was significantly lower than that of the other three groups. Furthermore, there was a significant difference between normals and unipolar patients, as determined by ANOVA. In particular, the fluorescence intensity ratio of the unipolar samples was significantly higher than that of the other three groups. These results are therefore useful in diagnosing unipolar (depressive) patients as well.

Example 10

Diagnosis of an Individual Patient as Bipolar

An individual patient's cell sample was tested as described herein and six to twelve ratios were calculated. These values were treated as a group and compared with a normal control group (negative control) and a bipolar group (positive control).

Tables 9 and 10 below present the statistics and the procedure employed for "Patient A." At the bottom of Table 9 there is pair wise comparison of these groups.

TABLE 9

One Way Analysis of Variance
Normality Test: Passed (P > 0.050)
Equal Variance Test: Passed (P = 0.050)

| Group Name | N | Missing | Mean | Std Dev | SEM |
|---|---|---|---|---|---|
| Controls | 173 | 0 | 0.850 | 0.0290 | 0.00220 |
| Bipolars | 178 | 0 | 0.768 | 0.0300 | 0.00225 |
| Patient A | 12 | 0 | 0.766 | 0.0125 | 0.00359 |

| Source of Variation | DF | SS | MS | F | P |
|---|---|---|---|---|---|
| Between Groups | 2 | 0.613 | 0.306 | 360.229 | <0.001 |
| Residual | 360 | 0.306 | 0.000850 | | |
| Total | 362 | 0.919 | | | |

The differences in the mean values among the treatment groups are greater than would be expected by chance; there is a statistically significant difference (P = <0.001).
Power of performed test with alpha = 0.050: 1.000
All Pairwise Multiple Comparison Procedures (Holm-Sidak method):
Overall significance level = 0.05

TABLE 9-continued

| | Comparisons for factor: | | | | |
|---|---|---|---|---|---|
| Comparison | Diff of Means | t | Unadjusted P | Critical Level | Significant? |
| Controls vs Bipolars | 0.0821 | 26.372 | 0.000 | 0.017 | Yes |
| Controls vs Patient A | 0.0844 | 9.699 | 0.000 | 0.025 | Yes |
| Bipolars vs Patient A | 0.00233 | 0.268 | 0.789 | 0.050 | No |

TABLE 10

Descriptive Statistics:

| Column | Size | Missing | Mean | Std Dev | Std. Error | C.I. of Mean |
|---|---|---|---|---|---|---|
| Controls | 173 | 0 | 0.850 | 0.0290 | 0.00220 | 0.00435 |
| Bipolars | 178 | 0 | 0.768 | 0.0300 | 0.00225 | 0.00444 |
| Patient A | 12 | 0 | 0.766 | 0.0125 | 0.00359 | 0.00791 |

| Column | Range | Max | Min | Median | 25% | 75% |
|---|---|---|---|---|---|---|
| Controls | 0.180 | 0.929 | 0.749 | 0.850 | 0.829 | 0.869 |
| Bipolars | 0.164 | 0.830 | 0.667 | 0.773 | 0.752 | 0.790 |
| Patient A | 0.0394 | 0.787 | 0.748 | 0.763 | 0.755 | 0.777 |

| Column | Skewness | Kurtosis | K-S Dist. | K-S Prob. | Sum | Sum of Squares |
|---|---|---|---|---|---|---|
| Controls | 0.0895 | 0.607 | 0.0400 | 0.661 | 147.073 | 125.176 |
| Bipolars | −0.601 | 0.187 | 0.0742 | 0.018 | 136.709 | 105.156 |
| Patient A | 0.347 | −1.092 | 0.138 | 0.665 | 9.188 | 7.037 |

As shown in Tables 9 and 10 above, there was a significant difference between controls and the patient. However, there was no significant difference between the patient and the bipolar group. From this, Patient A was diagnosed as bipolar.

Figure 15:
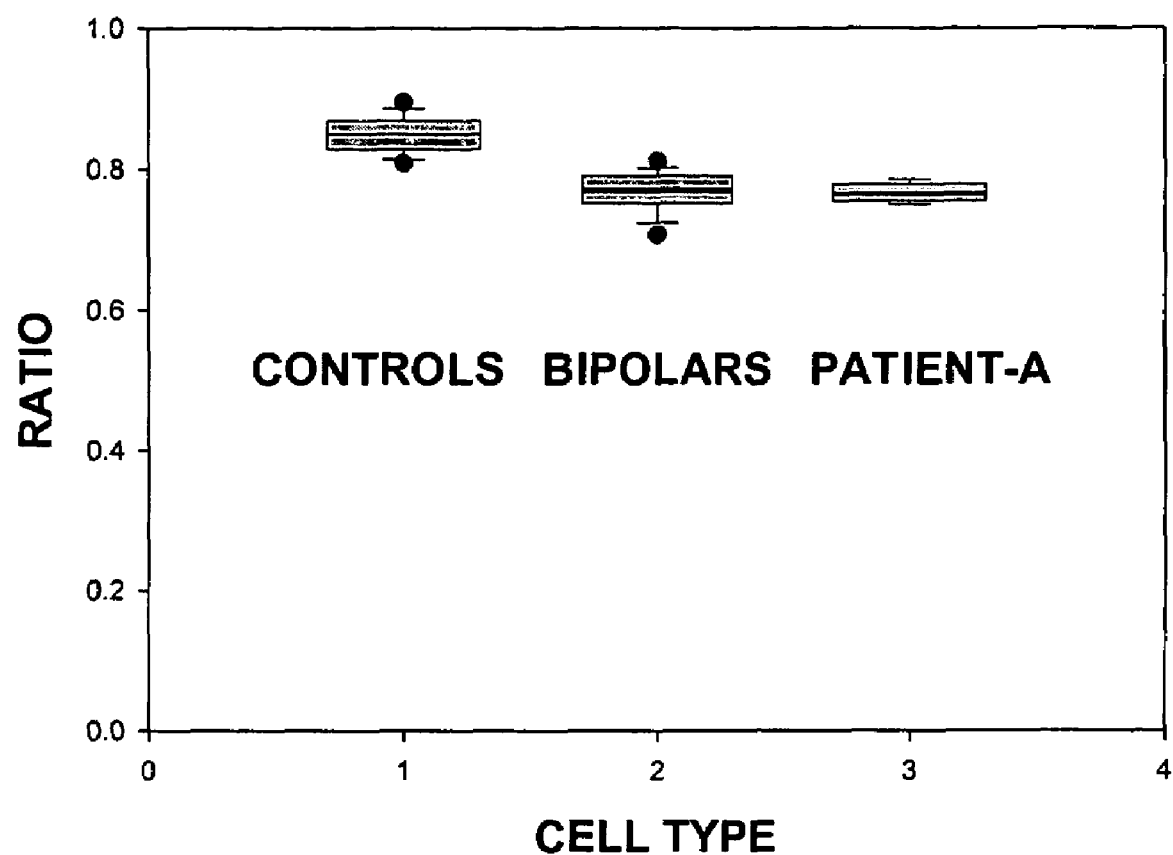
FIG. 15 provides an example of the use of ANOVA in the diagnosis of a representative patient ("Patient A") as bipolar. The ratio of fluorescence intensities and therefore membrane potentials in $K^+$-free buffer containing 30 µM ethacrynate was compared to the fluorescence intensity in $K^+$-containing buffer without ethacrynate.

FIG. 15 graphically depicts an example of the use of ANOVA in the diagnosis of Patient A as bipolar. The ratio of fluorescence intensities and therefore membrane potentials in $K^+$-free buffer containing 30 μM ethacrynate was compared to the fluorescence intensity in $K^+$-containing buffer without ethacrynate. The fluorescence intensity ratio of the patient's cell sample was significantly lower than that of the controls, but was not significantly different from that of the bipolars.

Example 11

Diagnosis of an Individual Patient as Unipolar

An individual patient's cell sample is tested as described herein and six to twelve ratios are calculated. These values are treated as a group and compared with a normal control group (negative control) and a unipolar group (positive control), in a manner similar to that described above in Example 10 for diagnosing an individual patient as bipolar.

The ratio of fluorescence intensities and therefore membrane potentials in $K^+$-free buffer containing 30 μM ethacrynate are compared to the fluorescence intensity in $K^+$-containing buffer without ethacrynate.

A patient is diagnosed as unipolar when there is a significant difference between controls and the patient (i.e., the fluorescence intensity ratio of the patient's cell sample is significantly higher than that of the controls) and/or there is no significant difference between the unipolar group and the patient. ANOVA is used in the diagnosis of a patient as unipolar.

Example 12

Specificity and Sensitivity of the Diagnostic Whole Blood Tests

Specificity is the ability to identify those who do not have the disease (Dawson et al, "Basic and Clinical Biostatistics", Third Edition, Lange Medical Books/McGraw-Hill, New York (2002)). As shown below in Table 11, the specificity in identifying controls was 100% in the blind trials described above in Example 9. Out of a control population (those with no known mental illness) of 18, all were diagnosed as negative for a bipolar disorder. The specificity for the overall non-bipolar (including schizophrenics and unipolars) population of 39 was 85% (33 out of 39) in the above-described blind trials. Among the schizophrenic patients, the test diagnosed 8 out of 10 correctly, indicating a specificity of 80% in the above-described blind trials. The specificity for the unipolar patients was 64% (seven out of eleven) in the above-described blind trials.

Sensitivity is defined as a test's ability to detect a disease among patients who actually have the disease (Dawson et al, supra). In the above-described blind trials, among the population of 20 bipolar patients (which were determined according to examination using the DSM IV), 14 were true positives. Hence the sensitivity of the test was 70%. However, doubts about the accuracy of DSM IV-based diagnoses of a bipolar disorder make the estimate of sensitivity unclear.

Consideration was given to whether patients on lithium and patients with diabetes during the blood draw could generate false diagnoses. Of the true positives, one patient was on lithium and 2 were diabetic. Of the false negatives, 2 patients were on lithium and 4 were diabetic. Lithium and diabetes did not have an effect on false positives and true negatives. Thus, lithium and diabetes did not appear to play a role on these tests.

TABLE 11

Summary Of Blind Tests For Bipolar Disorder

| | |
|---|---|
| Total samples tested: | 59 |
| Total positives: | 20 |
| Total negatives: | 39 |
| Diagnostic Blind Test Results | |
| Total negatives | 39 |
| True negatives | 33 |
| Specificity | 85% |
| Total controls | 18 |
| True controls | 18 |
| Specificity | 100% |
| Total schizophrenics | 10 |
| True schizophrenics | 8 |
| Specificity | 80% |
| Total unipolars | 11 |
| True unipolars | 7 |
| Specificity | 64% |
| Total bipolars | 20 |
| True positives | 14 |
| Sensitivity | 70% |

While the invention has been described in detail and with reference to specific embodiments thereof, it will be apparent to one skilled in the art that various changes and modifications can be made therein without departing from the spirit and scope thereof. All such obvious and foreseeable changes and modifications are intended to be encompassed by the following claims.

What is claimed is:

1. A method for diagnosing a bipolar disorder in a human patient, comprising:
   (a) obtaining a ratio of
      (i) the mean membrane potential of cells of a test human patient incubated in vitro in the presence of a compound that alters $Na^+K^+$ ATPase activity, but in the absence of $K^+$, to
      (ii) the mean membrane potential of cells of the test human patient incubated in vitro in the absence of the compound that alters $Na^+K^+$ ATPase activity, but in the presence of $K^+$; and
   one or both of the following steps (b) and (c):
   (b) comparing the ratio obtained in (a) to a control ratio, wherein the control ratio is the ratio of
      (iii) the mean membrane potential of corresponding control cells of one or more humans known to not have said bipolar disorder incubated in vitro in the presence of a compound that alters $Na^+K^+$ ATPase activity, but in the absence of $K^+$, to
      (iv) the mean membrane potential of corresponding control cells of one or more humans known to not have said bipolar disorder incubated in vitro in the absence of the compound that alters $Na^+K^+$ ATPase activity, but in the presence of $K^+$,
   wherein when the ratio obtained in (a) is significantly lower than the control ratio obtained in (b), said test human patient is diagnosed as having said bipolar disorder;
   (c) comparing the ratio obtained in (a) to a bipolar control ratio, wherein the bipolar control ratio is the ratio of
      (v) the mean membrane potential of corresponding bipolar control cells of one or more humans known to have said bipolar disorder incubated in vitro in the presence of a compound that alters $Na^+K^+$ ATPase activity, but in the absence of $K^+$, to
      (vi) the mean membrane potential of corresponding bipolar control cells of one or more humans known to have said bipolar disorder incubated in vitro in the absence of the compound that alters $Na^+K^+$ ATPase activity, but in the presence of $K^+$,
   wherein when the ratio obtained in (a) is not significantly different than the bipolar control ratio obtained in (c), said test human patient is diagnosed as having bipolar disorder
   wherein each mean membrane potential is determined by incubating the cells in vitro in buffer comprising a potential-sensitive dye, resuspending the cells in potential-sensitive dye free-buffer, and measuring cell fluorescence.

2. The method according to claim 1, wherein the compound that alters $Na^+K^+$ ATPase activity is selected from the group consisting of: valinomycin, monensin, monensin decyl ester, p-chloromercurybenzenesulfonate (PCMBS), veratridine, ethacrynate, dopamine, a catecholamine, a phorbol ester, ouabain, lithium, valproate, lamotrigine, cocaine, nicotine, RO-31-8220, oxymetazoline, calcineurin, topiramate, a peptide hormone, sorbitol, and a diuretic.

3. The method according to claim 2, wherein the compound that alters $Na^+K^+$ ATPase activity is ethacrynate.

4. The method of claim 1, wherein said bipolar disorder is bipolar I disorder.

* * * * *